US012533506B2

(12) United States Patent
Crosson et al.

(10) Patent No.: US 12,533,506 B2
(45) Date of Patent: *Jan. 27, 2026

(54) METHOD AND APPARATUS FOR INJURY TREATMENT

(71) Applicant: TRUERELIEF, LLC, Santa Monica, CA (US)

(72) Inventors: John Crosson, Santa Monica, CA (US); Herminio Llevat, Santa Monica, CA (US)

(73) Assignee: TrueRelief, LLC, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/409,646

(22) Filed: Jan. 10, 2024

(65) Prior Publication Data

US 2024/0139500 A1 May 2, 2024

Related U.S. Application Data

(63) Continuation of application No. 17/193,725, filed on Mar. 5, 2021, now Pat. No. 11,911,605.

(51) Int. Cl.
*A61N 1/36* (2006.01)
*A61N 1/04* (2006.01)

(52) U.S. Cl.
CPC ......... *A61N 1/0456* (2013.01); *A61N 1/0492* (2013.01); *A61N 1/36021* (2013.01)

(58) Field of Classification Search
CPC . A61N 1/0456; A61N 1/0492; A61N 1/36021
See application file for complete search history.

(56) References Cited

U.S. PATENT DOCUMENTS 945,564 A 1/1910 Marko
4,014,347 A 3/1977 Halleck
(Continued)

FOREIGN PATENT DOCUMENTS

AU 2020200898 2/2020
CA 2774272 3/2010
(Continued)

OTHER PUBLICATIONS

Notice of Allowance corresponding to Japanese Patent Application No. 2013-542044, Japanese Patent Office, dated May 17, 2016 (5 pages).
(Continued)

*Primary Examiner* — Alyssa M Alter
(74) *Attorney, Agent, or Firm* — ICE MILLER LLP; Justin D. Swindells

(57) ABSTRACT

An electrical stimulation apparatus provides an electrical stimulation signal as a DC pulse train at a frequency between 20 kHz and 50 kHz, with the electrical stimulation signal applied to the body of a patient at an injury site, based on sequentially activating respective subsets among a set of electrodes included in an electrode carrier that places the electrodes in contact with the body of the patient. An electrical stimulation method sequentially activates, via an electrical stimulation signal, respective subsets of electrodes among a set of electrodes contacting the body of a patient at an injury site on the body of the patient. Advantageously, in one or more embodiments, the sequential activation follows an activation sequence that "moves" the sources and sinks for the electrical stimulation signal around the injury site, thereby creating spatially distributed signal paths through or across the injury over time.

20 Claims, 16 Drawing Sheets

(56) References Cited

U.S. PATENT DOCUMENTS

| | | | |
|---|---|---|---|
| 4,112,923 | A | 9/1978 | Tomecek |
| 4,173,741 | A | 11/1979 | Kameny |
| 4,315,503 | A | 2/1982 | Ryaby |
| 4,319,584 | A | 3/1982 | McCall |
| 4,376,901 | A | 3/1983 | Pettibone |
| 4,455,527 | A | 6/1984 | Singer |
| 4,714,886 | A | 12/1987 | Halpern |
| 4,769,881 | A | 9/1988 | Pedigo |
| 4,926,865 | A | 5/1990 | Oman |
| 4,977,895 | A | 12/1990 | Tannenbaum |
| 5,045,988 | A | 9/1991 | Gritter |
| 5,109,847 | A | 5/1992 | Liss |
| 5,231,354 | A | 7/1993 | Leunbach |
| 5,304,211 | A | 4/1994 | Israel |
| 5,343,869 | A | 9/1994 | Pross |
| 5,347,221 | A | 9/1994 | Rubinson |
| 5,505,932 | A | 4/1996 | Grinstaff |
| 5,517,119 | A | 5/1996 | Weinstock |
| 5,571,149 | A | 11/1996 | Liss |
| 5,573,552 | A | 11/1996 | Hansjurgens |
| 5,584,863 | A | 12/1996 | Rauch |
| 5,592,086 | A | 1/1997 | Weinstock |
| 5,645,526 | A | 7/1997 | Flower |
| 5,674,261 | A | 10/1997 | Smith |
| 5,723,001 | A | 3/1998 | Pilla |
| 5,814,078 | A | 9/1998 | Zhou |
| 5,865,746 | A | 2/1999 | Murugesan |
| 5,900,227 | A | 5/1999 | Janzen |
| 5,945,564 | A | 8/1999 | Takayanagi |
| 6,110,106 | A | 8/2000 | Mackinnon |
| 6,140,346 | A | 10/2000 | Andrulis, Jr. |
| 6,157,854 | A | 12/2000 | Haber |
| 6,238,425 | B1 | 5/2001 | Thiberg |
| 6,242,919 | B1 | 6/2001 | Zuk |
| 6,302,900 | B1 | 10/2001 | Riggs |
| 6,319,682 | B1 | 11/2001 | Hochman |
| 6,335,625 | B1 | 1/2002 | Bryant |
| 6,430,430 | B1 | 8/2002 | Gosche |
| 6,461,375 | B1 | 10/2002 | Baudry |
| 6,465,507 | B2 | 10/2002 | Tang |
| 6,495,601 | B1 | 12/2002 | Hochman |
| 6,496,725 | B2 | 12/2002 | Kamada |
| 6,566,874 | B1 | 5/2003 | Speier |
| 6,573,063 | B2 | 6/2003 | Hochman |
| 6,594,527 | B2 | 7/2003 | Mo |
| 6,633,779 | B1 | 10/2003 | Schuler |
| 6,671,540 | B1 | 12/2003 | Hochman |
| 6,689,806 | B1 | 2/2004 | Tang |
| 6,706,709 | B2 | 3/2004 | Tang |
| 6,751,506 | B2 | 6/2004 | Shealy |
| 6,766,202 | B2 | 7/2004 | Underwood |
| 6,775,573 | B2 | 8/2004 | Schuler |
| 6,776,573 | B2 | 8/2004 | Arilla |
| 6,836,114 | B2 | 12/2004 | Reddy |
| 6,845,262 | B2 | 1/2005 | Albert |
| 6,974,415 | B2 | 12/2005 | Cerwin |
| 7,002,147 | B1 | 2/2006 | Hansknecht |
| 7,010,356 | B2 | 3/2006 | Jog |
| 7,058,446 | B2 | 6/2006 | Schuler |
| 7,082,325 | B2 | 7/2006 | Hashimshony |
| 7,092,760 | B2 | 8/2006 | Foster |
| 7,117,034 | B2 | 10/2006 | Kronberg |
| 7,150,710 | B2 | 12/2006 | Haber |
| 7,158,004 | B2 | 1/2007 | Ahn |
| 7,174,213 | B2 | 2/2007 | Pless |
| 7,198,776 | B2 | 4/2007 | Klaveness |
| 7,483,734 | B2 | 1/2009 | Colthurst |
| 7,574,257 | B2 | 8/2009 | Rittman, III |
| 7,603,171 | B2 | 10/2009 | Eror |
| 7,613,517 | B2 | 11/2009 | Goroszeniuk |
| 7,801,585 | B1 | 9/2010 | Weinstock |
| 7,847,644 | B2 | 12/2010 | Suzuki |
| 8,108,047 | B2 | 1/2012 | Schumann |
| 9,079,029 | B2 | 7/2015 | Weinstock |
| 9,149,386 | B2 | 10/2015 | Fahey |
| 9,238,138 | B2 | 1/2016 | Lee |
| 9,308,363 | B2 | 4/2016 | Goroszeniuk |
| 9,737,709 | B2 | 8/2017 | Bachinski |
| 10,130,805 | B2 | 11/2018 | Schonenberger |
| 10,252,053 | B2 | 4/2019 | Page |
| 10,499,848 | B2 | 12/2019 | Weinstock |
| 10,561,839 | B2 | 2/2020 | Wong |
| 10,960,207 | B2 | 3/2021 | Wong |
| 11,198,000 | B2 | 12/2021 | Crosson |
| 11,911,605 | B2 * | 2/2024 | Crosson ............... A61N 1/0468 |
| 2001/0039375 | A1 | 11/2001 | Lee |
| 2002/0042427 | A1 | 4/2002 | Tang |
| 2002/0052369 | A1 | 5/2002 | Tang |
| 2002/0055092 | A1 | 5/2002 | Hochman |
| 2003/0083724 | A1 | 5/2003 | Jog |
| 2003/0130709 | A1 | 7/2003 | D C |
| 2004/0015188 | A1 | 1/2004 | Coulter |
| 2005/0027333 | A1 | 2/2005 | Lennox |
| 2005/0033381 | A1 | 2/2005 | Carter |
| 2005/0158285 | A1 | 7/2005 | Giampapa |
| 2005/0165459 | A1 | 7/2005 | Coulter |
| 2005/0177201 | A1 | 8/2005 | Freeman |
| 2005/0177202 | A1 | 8/2005 | Classen |
| 2005/0197555 | A1 | 9/2005 | Mouradian |
| 2006/0052720 | A1 | 3/2006 | Ross |
| 2007/0060800 | A1 | 3/2007 | Drinan |
| 2007/0106342 | A1 | 5/2007 | Schumann |
| 2007/0129759 | A1 | 6/2007 | Colthurst |
| 2007/0179585 | A1 | 8/2007 | Chandler |
| 2008/0109049 | A1 | 5/2008 | Schumann |
| 2008/0183098 | A1 | 7/2008 | Denison |
| 2009/0149732 | A1 | 6/2009 | Weinstock |
| 2009/0270952 | A1 | 10/2009 | Weinstock |
| 2010/0204752 | A1 | 8/2010 | Tremblay |
| 2010/0324627 | A1 | 12/2010 | Weinstock |
| 2011/0166622 | A1 | 7/2011 | Crosson |
| 2013/0172838 | A1 | 7/2013 | Tremblay |
| 2017/0361095 | A1 | 12/2017 | Mueller |
| 2018/0289971 | A1 * | 10/2018 | Yeh .................... A61N 1/37229 |
| 2019/0008410 | A1 | 1/2019 | Crosson |
| 2019/0388278 | A1 | 12/2019 | Donda |
| 2020/0077943 | A1 | 3/2020 | Weinstock |
| 2021/0008369 | A1 | 1/2021 | Crosson |
| 2021/0128906 | A1 | 5/2021 | Perez |
| 2021/0379379 | A1 | 12/2021 | Campean |
| 2022/0080196 | A1 | 3/2022 | Crosson |

FOREIGN PATENT DOCUMENTS

| | | | |
|---|---|---|---|
| DE | 2443913 | | 4/1976 |
| EP | 0662311 | | 7/1995 |
| EP | 1537893 | | 6/2005 |
| GB | 2434544 | A | 8/2007 |
| JP | H10509600 | | 9/1998 |
| JP | 2001187035 | | 7/2001 |
| JP | 2003062034 | | 3/2003 |
| JP | 2004243047 | | 9/2004 |
| JP | 2010534114 | | 11/2010 |
| WO | 9610440 | A | 4/1996 |
| WO | 03076009 | A1 | 9/2003 |
| WO | 2005118061 | A | 12/2005 |
| WO | 2007075410 | A2 | 7/2007 |
| WO | 2007088348 | A2 | 8/2007 |
| WO | 2010031055 | A1 | 3/2010 |
| WO | 2011106225 | A2 | 9/2011 |
| WO | 2017156340 | A1 | 9/2017 |
| WO | 2020252406 | A1 | 12/2020 |

OTHER PUBLICATIONS

International Search Report and Written Opinion in International Application No. PCT/US2009/056990, mailed Nov. 2, 2009 (7 pages).
International Search Report for PCT/US2011/061451, dated Jul. 25, 2012, 8 pages.
International Search Report and Written Opinion in International Application No. PCT/US2006/043582, mailed Mar. 26, 2007 (13 pages).

(56) References Cited

OTHER PUBLICATIONS

International Search Report and Written Opinion in International Application No. PCT/US2011/025162, mailed Oct. 31, 2011 (7 pages).
International Search Report and Written Opinion in International Application No. PCT/US2020/037625, mailed Oct. 6, 2020 (14 pages).
Engstrom, Stefan , "Resonances and Magnetic Field Detection in Biological Systems", Electricity and Magnetism in Biology and Medicine, Springer, Boston, MA, 1999, pp. 223-226.
Muehsam, David J, et al., "The Sensitivity of Cells and Tissues to Exogenous Fields: Dependence Upon Target System Initial State", Electricity and Magnetism in Biology and Medicine, edited by Bersani, Kluwer Academic/Plenum Publishers, 1999, pp. 405-408.
Peeters, A.M.G , "Single-rail handshake circuits", Technische Universiteit Eindhoven, https://doi.org/10.6100/IR461274, Jan. 1, 1996, 202 pages.
Pilla, Arthur A, "A Larmor Precession/Dynamical System Model Allows µt-Range Magnetic Field Effects on Ion Binding in the Presence of Thermal Noise", Electricity and Magnetism in Biology and Medicine, Edited by Bersani, Kluwer Academic/Plenum Publishers, 1999, 395-399.
Yasui, Mitsuru , et al., "Effect of Magnetic Field Exposure on Calcium Channel Currents Using Patch-Clamp Technique", Electricity and Magnetism in Biology and Medicine, Edited by Bersani, Kluwer Academic/Plenum Publishers, 1999, pp. 581-584.

* cited by examiner

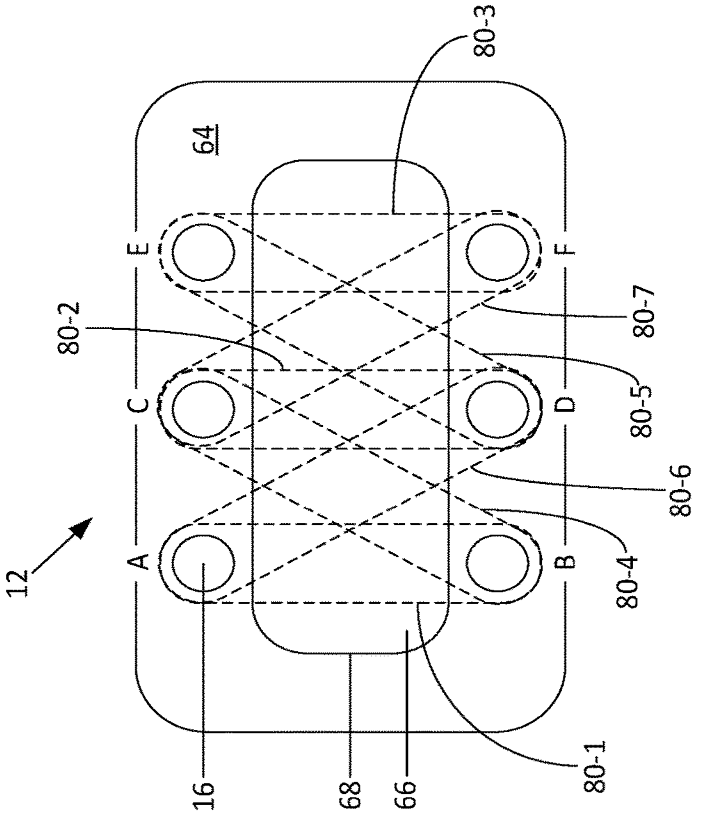
FIGURE 5
82
| PAIRS | SOURCE | SINK |
|---|---|---|
| 80-1 | A | B |
| 80-2 | C | D |
| 80-3 | E | F |
| 80-4 | B | C |
| 80-5 | D | E |
| 80-6 | A | D |
| 80-7 | C | F |
FIGURE 6
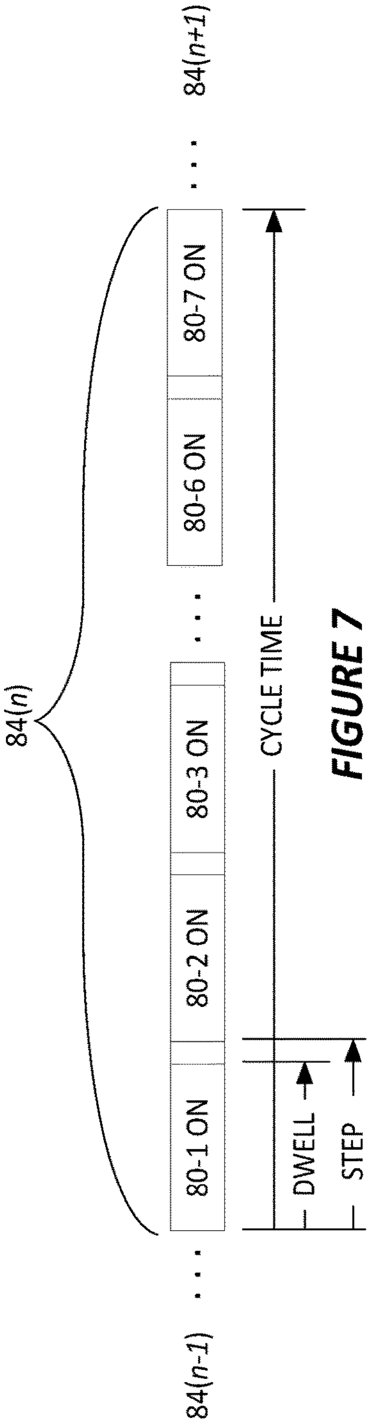
FIGURE 7

METHOD AND APPARATUS FOR INJURY TREATMENT

CROSS-REFERENCE TO RELATED APPLICATIONS

This application is a continuation of U.S. patent application Ser. No. 17/193,725 filed Mar. 5, 2021, the disclosure of which is incorporated herein by reference in its entirety.

TECHNICAL FIELD

An electrical stimulation apparatus and a method of electrical stimulation, for applying an electrical stimulation signal to a body of a patient at an injury site on the body of the patient.

BACKGROUND

Therapeutic application of electrical signals to the human body, sometimes referred to as "electrostimulation" or "electrical stimulation therapy," has a long history. Perhaps best known among contemporary, routine use of electrostimulation, Transcutaneous Electrical Nerve Stimulation (TENS) devices generate electrical impulses that are delivered through the skin, for relieving chronic or acute pain.

TENS signals characteristically range from below 10 Hz to as high as 400 Hz, with the intensity of the signal dependent on the involved frequency range and intended effect. For example, TENS signals below 10 Hz may have a higher intensity, for inducing motor contractions, while TENS signals above 50 Hz generally have lower intensities. However, other known electrostimulation devices operate at higher frequencies, or at least offer the capability to operate at higher frequencies. As one example, see U.S. Pat. No. 10,085,670 B2, issued on 2018 Oct. 2.

Wound healing represents another application of electrostimulation, with U.S. Pat. No. 7,520,849 B1, as issued on 2009 Apr. 21, offering one example. As one earlier example, see U.S. Pat. No. 4,846,181 A, issued on 1989 Jul. 11. U.S. Pat. Pub. 2010/0204752 A1 offers another example of electrostimulation applied in the context of wound healing, in combination with the use of negative pressure treatment.

The wide variation in electrostimulation device configurations and operational parameters seen in the field of electrostimulation reflects not only the wide range in intended uses, from pain relief to neuromuscular stimulation, but also continuing uncertainty about the parameters that are key for efficacy in any particular application. An acute need remains for electrostimulation devices and electrostimulation methods that yield high efficacy in the areas of pain relief and injury healing.

SUMMARY

An electrical stimulation apparatus provides an electrical stimulation signal as a DC pulse train at a frequency between 10 kHz and 50 kHz, with the electrical stimulation signal applied to the body of a patient at an injury site, based on sequentially activating respective subsets among a set of electrodes included in an electrode carrier that places the electrodes in contact with the body of the patient. An electrical stimulation method sequentially activates, via an electrical stimulation signal, respective subsets of electrodes among a set of electrodes contacting the body of a patient at an injury site on the body of the patient. Advantageously, in one or more embodiments, the sequential activation follows an activation sequence that "moves" the sources and sinks for the electrical stimulation signal in a scanning or circulating pattern around the injury site.

One embodiment of an apparatus configured for therapeutic electrical stimulation of a patient includes an electrode carrier and a stimulation module. The electrode carrier is configured to place a set of electrodes into contact with the body of the patient at an injury site on the body of the patient. Signal generation circuitry in the stimulation module is configured to generate an electrical stimulation signal as a Direct Current (DC) pulse train at a frequency of between 10 kHz and 50 kHz. Control circuitry in the stimulation module is configured to sequentially activate individual subsets of electrodes in the set of electrodes, each subset including one or more electrodes activated as a signal source for the electrical stimulation signal and one or more electrodes activated as a signal sink for the electrical stimulation signal.

Advantageously, in at least one embodiment of the apparatus, the sequential activation follows an activation sequence that "moves" the sources and sinks for the electrical stimulation signal around the injury site. Here, "moving" the signal sources and sinks does not mean physical movement; rather, it means changing which electrodes are active over time, according to a spatial pattern or sequence, such that the electrical stimulation signal is sourced/sunk from multiple positions around the injury at the injury site. Moving the signal sources and sinks create spatially distributed signal paths through or across the injury over time.

In a further advantageous arrangement used in at least one embodiment of the apparatus, the electrode carrier incorporates a ported chamber that is sealably closed with adherence of the electrode carrier on the body of the patient at the injury site. In such embodiments, the control circuitry is configured to control application of negative pressure via the electrode carrier in conjunction with controlling application of the electrical stimulation signal. The moving sources and sinks provided via the sequential electrode activation combine with negative pressure treatment, for synergistic application of injury-healing therapies.

In another embodiment, a method performed by an apparatus configured for therapeutic electrical stimulation of a patient includes the step or operation of providing an electrical stimulation signal as a DC pulse train at a frequency of between 10 kHz and 50 kHz. Further, the method includes sequentially activating respective subsets of electrodes among a set of electrodes contacting the body of the patient at an injury site on the body of the patient, via the electrical stimulation signal. For example, the sequential activation follows a defined activation sequence and activation cycle.

Of course, the present invention is not limited to the above features and advantages. Those of ordinary skill in the art will recognize additional features and advantages upon reading the following detailed description, and upon viewing the accompanying drawings.

BRIEF DESCRIPTION OF THE DRAWINGS

FIG. 5 is a diagram of further example activation patterns and activation subsets for electrodes in an electrode carrier.

FIGS. 6 and 7 are diagrams of example electrode activation sequences and activation cycles, according to one or more embodiments.

DETAILED DESCRIPTION

Figure 1:
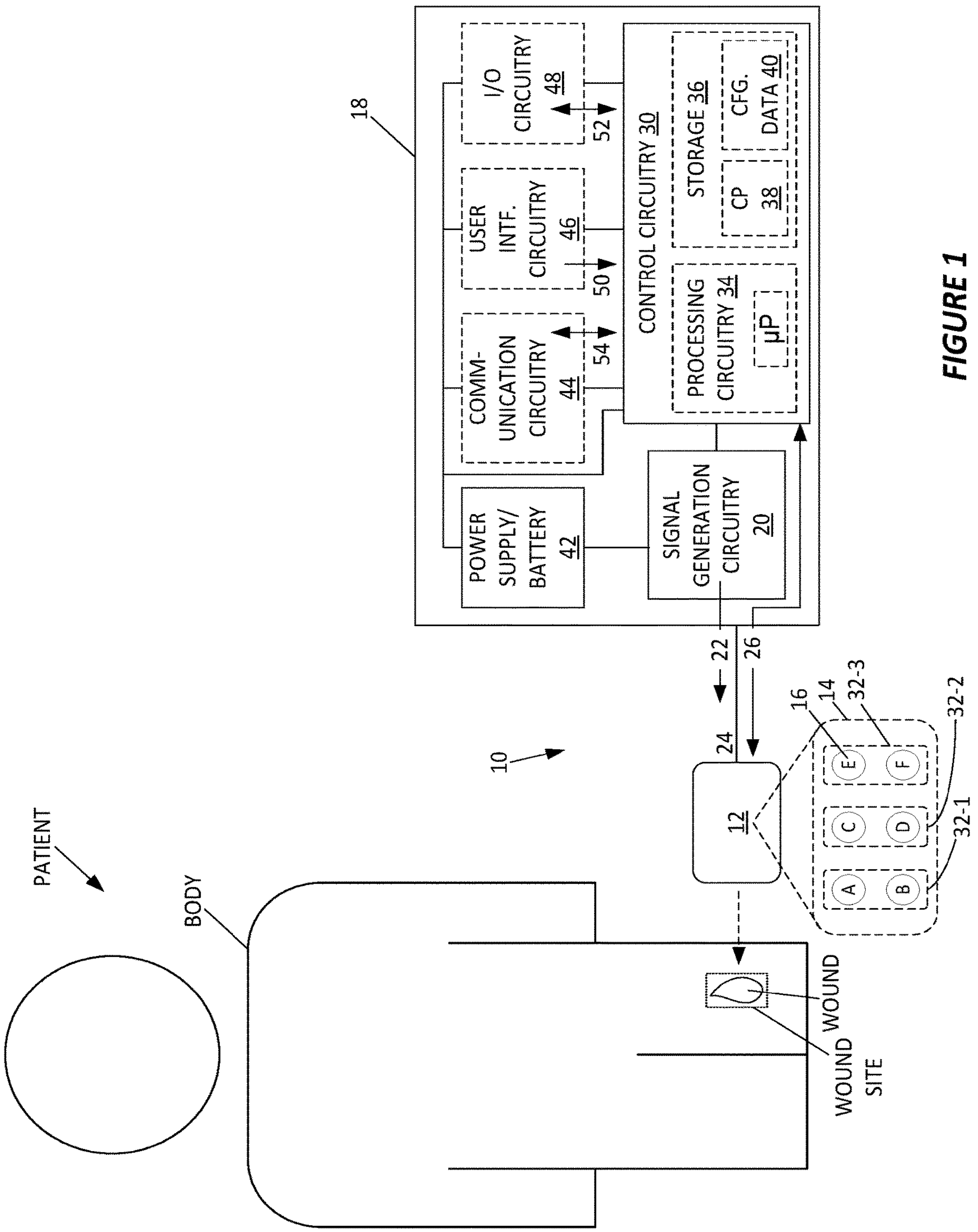
FIG. 1 is a block diagram of one embodiment of an apparatus configured for therapeutic electrical stimulation of a patient, the apparatus also referred to as an electrostimulation apparatus.

FIG. 1 depicts example details for one embodiment of an electrostimulation apparatus 10 (hereafter "apparatus 10") that is configured for therapeutic electrical stimulation of a patient. Although the diagram depicts a human patient, the term "patient" encompasses any living animal.

An electrode carrier 12 of the apparatus 10 includes a set 14 of electrodes 16, while a stimulation module 18 of the apparatus 10 includes signal generation circuitry 20 that is configured to generate an electrical stimulation signal 22 that is provided to respective electrodes 16 in the electrode carrier 12 via a wired or wireless connection 24. In at least some embodiments, one or more additional signals 26 go between the electrode carrier 12 and the stimulation module 18, such as for use by the stimulation module 18 in sensing or reading the type, model, or configuration of the electrode carrier 12, or in controlling which electrode(s) 16 are active at given times during electrostimulation therapy.

Control circuitry 30 in the stimulation module 18 controls electrode activation either directly via the signals 26, such as in embodiments where stimulation-signal generation occurs on the electrode carrier 12, or indirectly via control of the signal generation circuitry 20. For example, the connection 24 in one embodiment carries an electrical connection for each electrode 16 and the signal generation circuitry 20 "activates" respective subsets 32 of the electrodes 16 responsive to control signaling by the control circuitry 30.

Subsets 32-1, 32-2, and 32-3 appear in the diagram, but the example is non-limiting. There may be a smaller or a greater number of subsets 32, any given subset 32 may include more than two electrodes 16, and two or more subsets 32 may have one or more electrodes 16 in common. Further, the subsets 32 need not have the same number of members, e.g., one subset 32 may include two electrodes 16, while another subset 32 includes three electrodes 16, and so on.

Thus, while the subsets 32-1, 32-2, and 32-3 are shown as electrode pairs {A|B}, {C|D}, and {E|F}, other example subsets are {A|B, C}, {C|D, B, F}, etc. Here, electrodes 16 in the subset that are listed to the left of the "|" character operate as a signal source of the electrical stimulation signal 22, while electrodes 16 in the subset that are listed to the right of the "|" character operate as a signal sink of the electrical stimulation signal 22. With that understanding, the subset 32 formed as {A|B} distinguishes from the subset 32 formed as {B|A}.

One approach, noted above, for providing the control circuitry 30 with control of subset formation or activation relies on the connection 24 including an electrical connection for each electrode 16 carried by the electrode carrier 12. In an example implementation, the signal generation circuitry 20 includes a multiplexer that selectively connects one or more electrodes 16 as signal sources and one or more electrodes 16 as signal sinks, with the selective connectivity controlled by the control circuitry 30. In other embodiments, the signal generation circuitry 20 is programmed or arranged via fixed circuitry to activate predefined subsets 32.

For example, the signal generation circuitry 20 in one or more embodiments is configured to activate/deactivate individual ones of the electrodes 16 and to control whether a given electrode 16 is activated as a signal source or a signal sink. With this arrangement, arbitrary subsets 32 may be formed from among the overall set 14 of electrodes 16 of the electrode carrier 12.

In yet other embodiments, circuitry on the electrode carrier 12 controls subset formation or activation, in dependence on signaling received from the stimulation module 18, with such arrangements reducing or eliminating the number of wires needed in wired versions of the connection 24. For example, the connection 24 in an example embodiment includes the positive and negative (or "ground") wires associated with sourcing and sinking the electrical stimulation signal 22, with one or more additional wires associated with the signaling 26, for controlling subset formation or activation on the electrode carrier 12. In yet other embodiments, the signaling 26 may include high-frequency signaling impressed on the electrical stimulation signal 22. In such embodiments, the electrode carrier 12 includes circuitry that is configured to detect or otherwise respond to the high-frequency signaling.

Other example details in the embodiment of the apparatus 10 illustrated in FIG. 1 include elements of the control circuitry 30, which include processing circuitry 34 and storage 36, such as may be used for the storage of one or more computer programs 38 or configuration data 40. Here, and elsewhere in the disclosure, the word "or" encompasses the conjunctive case, unless otherwise noted or otherwise clear from the context. That is, unless noted or excluded by the contextual usage, the phrase "A or B" means A singly, B singly, or both A and B.

The processing circuitry 34 comprises, for example, any one or more of one or more microprocessors, microcontrollers, Field Programmable Gate Arrays (FPGAs), Complex Programmable Logic Devices (CPLDs), Digital Signal Processors (DSPs), Application Specific Integrated Circuits (ASICs), or System-on-a-Chip (SoC) modules. Broadly, the processing circuitry 34 comprises fixed circuitry or programmatically-configured circuitry, or some mix of both.

In an example where the processing circuitry 34 comprises a microprocessor ("μP"), the microprocessor is, for example, a general-purpose microprocessor that is specially adapted to carry out the operations described herein for the apparatus 10, based at least in part on its execution of computer program instructions from one or more computer programs ("CP") 38 held in storage 36. That is, in one or more microprocessor-based embodiments of the apparatus 10, the execution of computer program instructions by the microprocessor causes the apparatus 10 to function as described herein.

Correspondingly, the storage 36 comprises one or more types of computer-readable media, such as one or more types of memory circuits or storage devices and may be in whole or in part integrated with the processing circuitry 34, or accessible to it. Non-limiting examples of memory circuits include volatile memory as working memory for "live" operation of the apparatus 10 and non-volatile memory for longer-term storage of program instructions and various parameter or settings values, referred to as configuration data ("CFG. DATA") 40. Volatile memory examples include SRAM or DRAM, while non-volatile memory examples include EEPROM, FLASH, and Solid State Disk (SSD).

Other example elements of the apparatus 10 include a power supply 42, which may include a battery, such as a lithium ion battery for portable operation of the apparatus 10. In an example implementation, the power supply 42 is configured for a mains power connection, e.g., electrical power at 50/60 Hz from 110 VAC to 250 VAC and includes one or more isolation transformers to foreclose the possibility of energizing the electrodes 16 with unsafe voltage or current levels. In general operation, the power supply 42 outputs one or more controlled supply signals, e.g., DC supply voltages at one or more voltage levels, for use by the various circuitry within the apparatus 10.

Examples of such other circuitry include communication circuitry 44, user interface circuitry 46, and input/output (I/O) circuitry 48. The communication, user interface, and I/O circuitry 44, 46, and 48 are shown in dashed boxes to indicate optional inclusion in one or more embodiments of the apparatus 10. Similarly, the processing circuitry 34 and storage 36, along with the CP 38 and CFG. DATA 40 are shown in dashed boxes to indicate that one or more embodiments of the apparatus 10 may not include them, such as where the control circuitry 30 exclusively relies on fixed circuitry for its implementation.

In one or more embodiments, the communication circuitry 44 provides wireless communications, such as for wireless communication with the electrode carrier 12 in one or more embodiments, or for wirelessly coupling the apparatus 10 to a WI-FI access point or other type of Wireless Local Area Network (WLAN). Additionally, or alternatively, the communication circuitry 44 implements Near Field Communication (NFC) or Personal Area Network (PAN) connectivity, such as for registering or reading the particular type, model, or configuration of the electrode carrier 12 to be used at any given time, with the electrode carrier 12 correspondingly incorporating complementary communications circuitry. PAN connectivity relies on, for example, BLUETOOTH communications.

In one or more embodiments, BLUETOOTH, WI-FI, or other wireless connectivity provided by the communication circuitry 44 provides for implementation of user control or monitoring of the apparatus 10, either via a local user having wireless connectivity to the apparatus 10 via a smartphone, tablet, laptop, or other computing device, or via a remote user connected via the Internet.

Further, in at least one embodiment of the apparatus 10 in which the communication circuitry 44 is included, the communication circuitry 44 includes one or more wired interfaces, such as an Ethernet connection supporting data networking of the apparatus 10. Of course, data network via WLAN connectivity may also be used, or other data-connections, such as a Serial Peripheral Interface (SPI), or another serial interface. With such connectivity, the apparatus 10 may receive configuration data, for example, to tailor patient treatment to a particular patient or to a particular treatment session for a particular patient and may output treatment confirmation records. Such records may include time/date stamps, patient name, or ID, along proof-of-treatment, such as a unique nonce generated by the control circuitry 30. All such data may be encrypted at rest or in communication.

In addition to user control being provided via a smartphone or other external computing device, or as addition or alternative to such arrangements, the apparatus 10 in one or more embodiments includes user interface circuitry 46 operative to provide user inputs—i.e., signals or data indicative of user actuations of user-interface elements or controls—to the control circuitry 30. Example user inputs include on/off control, activation/deactivation of stimulation-signal generation, treatment timing control, or the adjustment of operating parameters, such as adjustment inputs of one or more electrical parameters of the electrical stimulation signal 22 or the configuration of (electrode) subsets 32 or the configuration of the activation sequence or cycle used for activating the respective subsets 32. The reference number "50" denotes any and all such user-input signaling into the control circuitry 30.

The I/O circuitry 48, as included in at least one embodiment of the apparatus 10, provides, for example, a mass storage interface for reading and writing patient information regarding electrostimulation treatment via the apparatus 10. Additionally, or alternatively, the I/O circuitry 48 provides one or more discrete input or output lines, such as for interfacing with annunciators to indicate the start or completion of treatment via the apparatus 10.

With the above example details and implementation variations in mind, an apparatus 10 according to one or more embodiments includes an electrode carrier 12 that is configured to place a set 14 of electrodes 16 into contact with the body of the patient at an injury site on the body of the patient. Further included in the apparatus 10, a stimulation module 18 includes signal generation circuitry 20 that is configured to generate an electrical stimulation signal 22 as a Direct Current (DC) pulse train at a frequency of between 10 kHz and 50 kHz. The particular signal frequency may be fixed or adjustable.

Control circuitry 30 included in the stimulation module 18 is configured to sequentially activate individual subsets 32 of electrodes 16 in the set 14 of electrodes 16. Each subset 32 includes one or more electrodes 16 activated as a signal source for the electrical stimulation signal 22 and one or more electrodes 16 activated as a signal sink for the electrical stimulation signal 22.

Figure 2C:
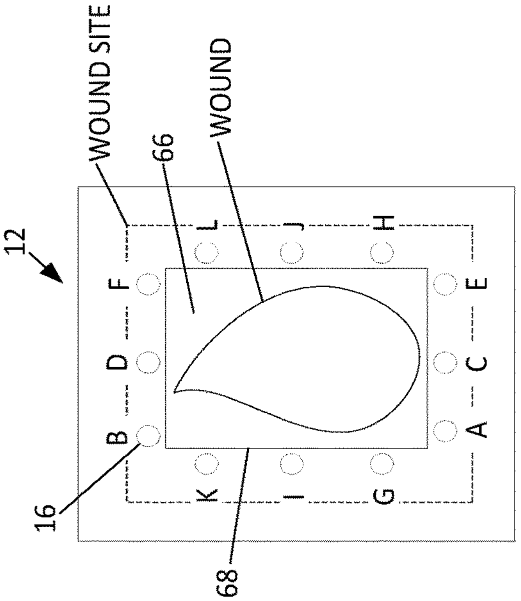
FIGS. 2A-2F are diagrams of example embodiments of an electrode carrier.
Figure 2A:
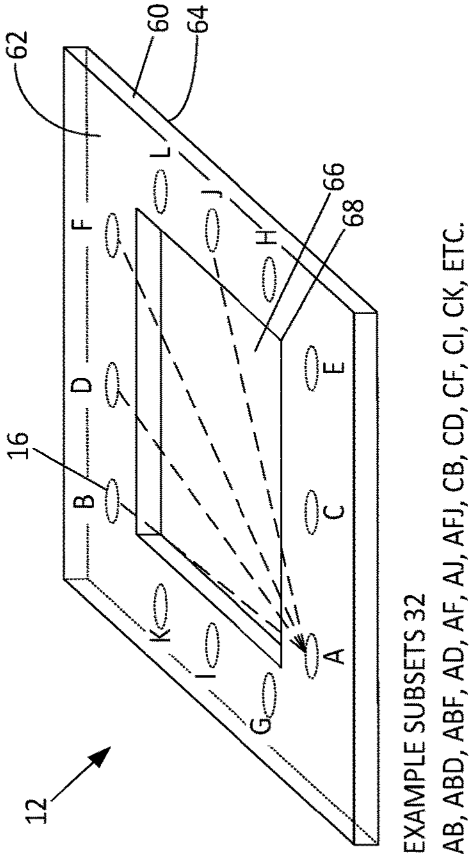

FIG. 2A illustrates an example embodiment of the electrode carrier 12, where the electrode carrier 12 comprises a flexible sheet or membrane 60 configured for conformable placement on the body of the patient at the injury site. The flexible sheet or membrane 60—hereafter "sheet 60"—has a top surface 62 facing away from the body of the patient and carries the set 14 of electrodes 16 on a patient-facing surface 64 of the flexible sheet 60. In one or more embodiments, the sheet 60 may comprise two or more plies, with the electrodes 16 and the associated electrode wiring embedded therein for durability and protection. Of course, the patient-contacting portion of the electrodes 16 is exposed on the bottom ply—i.e., exposed on the patient-facing surface 64 of the sheet 60. Another feature of the sheet 60 in one or more embodiments is oxygen permeability, meaning that the skin of the patient that is covered by the sheet 60 remains free to "breathe."

Figure 2B:
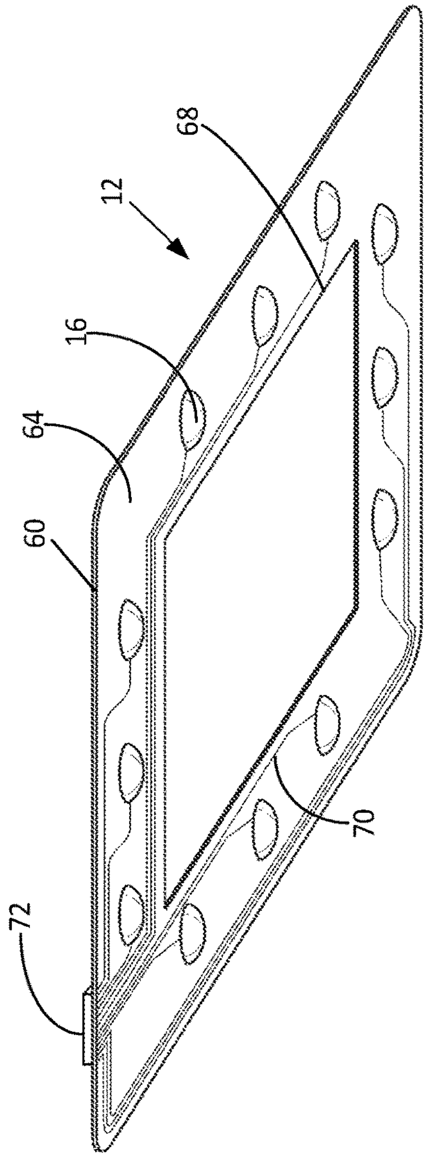

Because FIG. 2A provides a top-side perspective view of the electrode carrier 12, the electrodes 16 are shown in hidden-view dotted lines, denoting the possibility that the electrodes 16 (and their associated wiring) may be embedded within the flexible sheet 60 as described above and exposed only on the patient-facing surface 64, such as seen in FIG. 2B, where the individual electrodes 16 are hemispherical "buttons" or "nubs" that provide localized but comfortable contact points on the skin of the patient.

In one or more embodiments, the flexible sheet 60 includes a central cutout or opening 66 for leaving exposed an injury at the injury site on the body of the patient. Correspondingly, the set 14 of electrodes 16 are arrayed at spaced-apart locations along the edge or perimeter 68 defining the cutout or opening 66.

FIG. 2B illustrates another feature included in one or more embodiments of the electrode carrier 12; namely, the electrode carrier 12 may include printed or flexible, embedded conductors 70 for electrically connecting to each electrode 16, and may include an electrical connector 72, for quick and convenient connection to cabling going to the stimulation module 18. That is, in embodiments where the connection 24 between the electrode carrier 12 and the stimulation module 18 is a wired connection, a cable having a complementary connector may be used to electrically connect the electrode carrier 12 to the stimulation module 18.

Figure 2D:
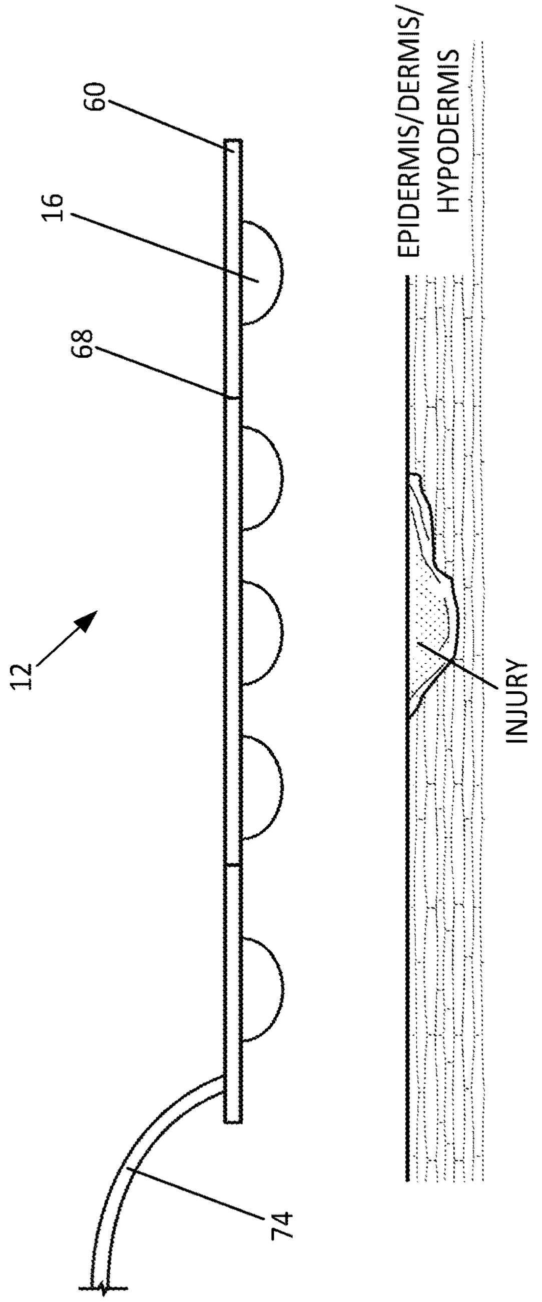
Figure 2E:
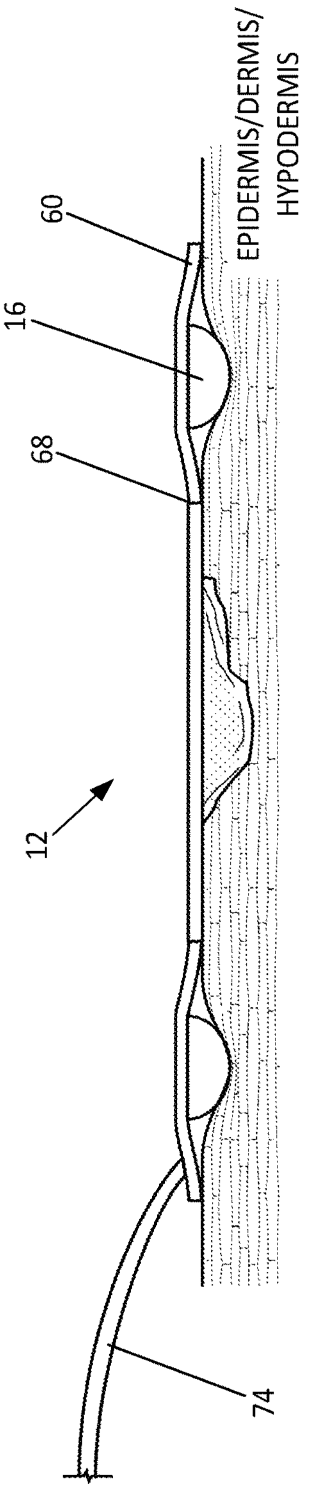

FIG. 2C illustrates same embodiment of the electrode carrier 12, depicted in situ in a surrounding arrangement with respect to an injury on the body of the patient. Particularly, the example injury is an open wound. Correspondingly, FIGS. 2D and 2E illustrate the same embodiment of the electrode carrier 12 before and after placement in the wound-surrounding arrangement. As seen in the side-view depictions provided in FIGS. 2D and 2E, the electrodes 16 slightly depress the skin of the patient at the point of contact, without breaking the skin and without exerting undue pressure. Also shown in FIGS. 2D and 2E is an example cable 74, for wired coupling back to the stimulation module 18 as the "connection 24" introduced in FIG. 1.

Figure 2F:
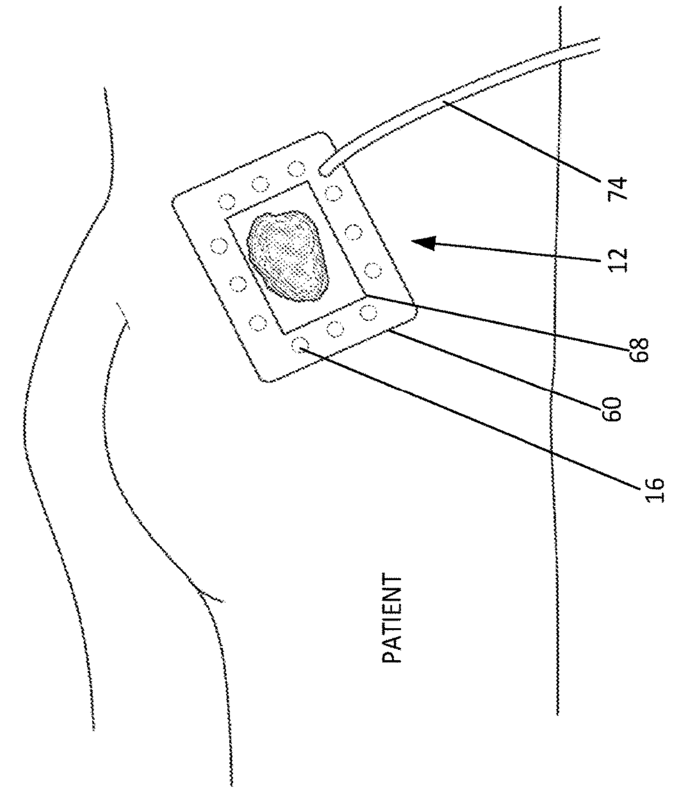

"Conformability" is one among the several advantages of using a flexible sheet 60 as the basis of the electrode carrier 12. FIG. 2F highlights the conformability advantage, showing the electrode carrier 12 applied to the lower torso of a patient, near the buttocks region, for treatment of a pressure sore or other injury.

Various embodiments of the electrode carrier 12 use some form of adhesive—either pre-applied on the patient-facing surface 64 of the sheet 60 or applied to the skin of the patient before applying the sheet 60. Other embodiments of the electrode carrier 12 use fasteners, straps, or elastic material, for fixing the electrode carrier 12 to the body of the patient.

The phrase "flexible sheet or membrane 60" denotes not only the possible implementation of the electrode carrier 12 as latex or other rubber or polymer sheet, with molded-in or embedded electrodes 16 and associated wiring/connectors, but also the possible implementation of the electrode carrier 12 as a woven fabric sheet or web. Of course, the electrode carrier 12 also may comprise a mix of fabric and rubber or polymer elements. At least the portion of the electrode carrier 12 that contacts the skin of the patient may be porous or non-porous.

Further, although FIGS. 2A-2F offer the example of a rectangular shape for the flexible sheet 60 and the cutout 66, that example is non-limiting. The sheet 60 may be ellipsoid, circular, arcuate, or irregularly shaped, for matching the electrode carrier 12 to various shapes or sizes of injuries, and to various bodily locations of injuries. In a contemplated arrangement, multiple shapes/types of electrode carriers 12 are provided, all being compatible with the stimulation module 18. With this approach, treating an injury includes an initial step of selecting the shape, size, or type of electrode carrier 12 that is best suited to the nature and location of the injury, or to the nature of the treatment desired. For example, electrostimulation for relief of tendonitis pain favors a particular type or style of electrode carrier 12, as opposed to what would be used for electrostimulation of an open wound for pain relief and tissue regeneration.

Treatment benefits may be particularly pronounced with respect to invasive injuries that involve openings or cuts in the skin of the patient, such as burns, ulcers, surgical excisions, or incisions, etc. Such benefits include but are not limited to pain relief, faster healing, and reduced scarring. However, use of the apparatus 10 is not limited to treatment of invasive injuries. For example, in one or more embodiments, the apparatus 10 is configured for the treatment of closed injuries, such as muscle tears or inflammatory conditions. Thus, the word "injury" has broad meaning herein. Correspondingly, not all embodiments of the electrode carrier 12 include a cutout 66, and one or more embodiments carry the set of electrodes 16 as a rectangular grid or other arrayed pattern that provides a uniformly or non-uniformly spaced set of electrode contact points across a corresponding region of skin on the body of the patient.

Figure 3:
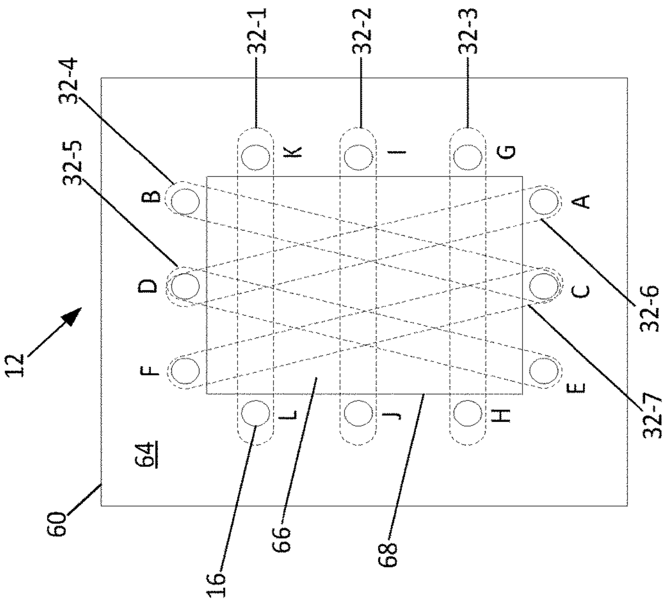
FIG. 3 is a diagram of example activation patterns and activation subsets for electrodes in an electrode carrier.

In the example of FIG. 3, the set 14 of electrodes 16 includes electrodes 16 labeled as electrodes A-L, with these electrodes 16 arrayed at spaced apart positions in a surrounding arrangement with respect to a central cutout 66 in a sheet 60 serving as the base element of the electrode carrier 12. Particularly, the cutout 66 leaves the involved injury exposed, which may help with comfort and healing for certain types of injuries, while the electrodes 16 form an array along the perimeter or edge 68 of the cutout 66. With proper sizing or selection of the electrode carrier 12 with respect to the injury size or shape, such an arrangement positions the set 14 of electrodes 16 such that one or more subsets 32 of electrodes 16 are bridging with respect to the injury.

Any number of subsets 32 may be formed, with FIG. 3 showing specific subsets 32-1, 32-2, through 32-7. By way of example, the subset 32-1 comprises {K|L} (or {L|K}, the subset 32-2 comprises {I|J} (or {J|I}, and so on. A "treatment" of the patient with respect to the example electrode subsets depicted in FIG. 3 comprises, for example, sequentially activating two or more subsets 32 according to a defined activation sequence, over one or more activation cycles. While the activation sequence may exercise all possible permutations of source/sink electrodes available via the set 14 of electrodes 16 provided by the electrode carrier 12, fewer subsets 32 may be used/defined by the activation sequence and different treatment regimens may use different subsets 32 and different activation timings or overall treatment time.

Figure 4A:
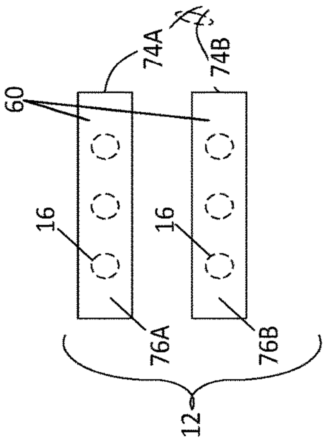
FIGS. 4A-4C are diagrams of further example embodiments of an electrode carrier.

FIG. 4A illustrates another embodiment of the electrode carrier 12, where the sheet 60 is divided into two pieces or parts, which may or may not be interconnected together. In the illustrated example, the sheet 60 comprises two strips 76A and 76B, each carrying a number of electrodes 16. The strip 76A may be placed on one "side" of an injury, with the strip 76B placed on the opposing/other side of the injury, with the respective strips 76A and 76B coupled to the stimulation module 18 via cables 74A and 74B, which may nonetheless be consolidated into a single cable with a "Y" arrangement at the strips 76A and 76B.

Notably, the strips 76A and 76B may be of any length and may be linear, arcuate, or irregularly shaped, for maximum flexibility with respect to matching the size of an injury. In some embodiments, the strips 76A and 76B may be cut to length and in other embodiments they are provided in predetermined lengths. Moreover, in at least one embodiment, the stimulation module 18 is configured to operate with up to N (N>1) individual electrode strips 76 collectively operating as the electrode carrier 12, meaning that a multiplicity of electrode strips 76 may be placed at an injury site on the body of the patient in a generally surrounding arrangement with respect to the injury.

In some embodiments, or according to some treatment protocols, the electrodes 16 contact the skin just off from the injury itself—periwound skin bordering an open wound, for example. In other embodiments or treatment protocols, one or more of the electrodes 16 contact the surface of the wound, which can be helpful particularly with deep, ulcerative wounds. In at least one embodiment, one or more of the electrodes 16 is configured as a "flying" electrode, e.g., it extends from the electrode carrier 12 via a lead extension, allowing it to be placed strategically on or within the wound, while other ones of the electrodes 16 contact the skin on one or more "sides" of the wound.

Figure 4B:
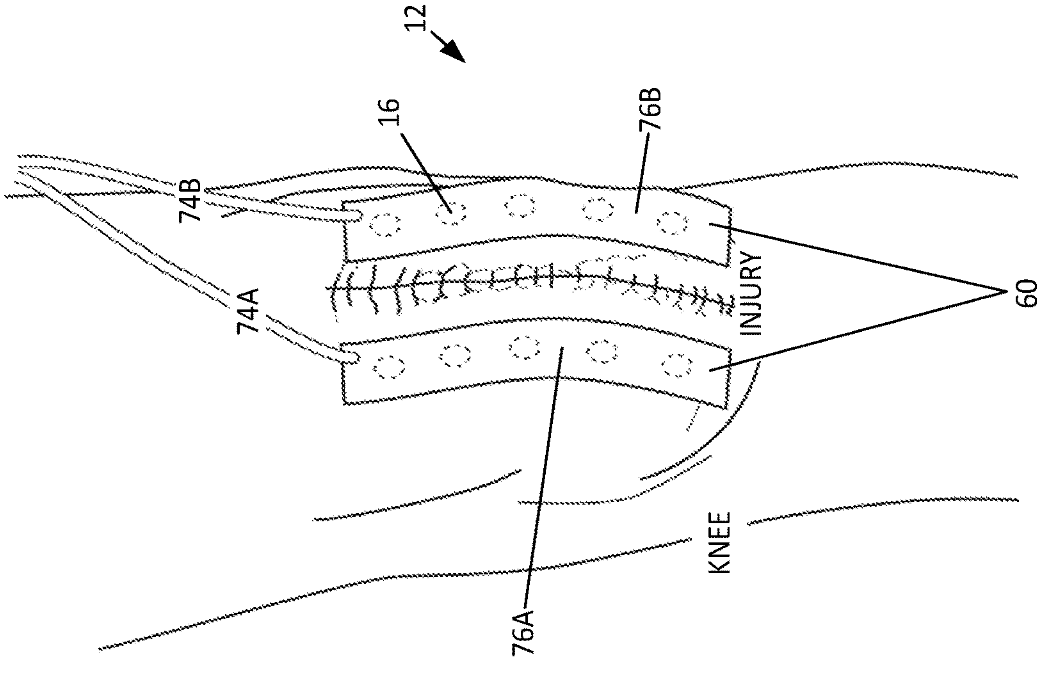

FIG. 4B illustrates an example use of a strip-based embodiment of the electrode carrier 12, wherein two strips 76A and 76B are attached to the skin of a (human) patient along either side of a surgical incision at the knee of the patient. The strips 76A and 76B may be applied/fixed to the skin using adhesive, for example, or may be held in place via an elastic wrap or the like.

Figure 4C:
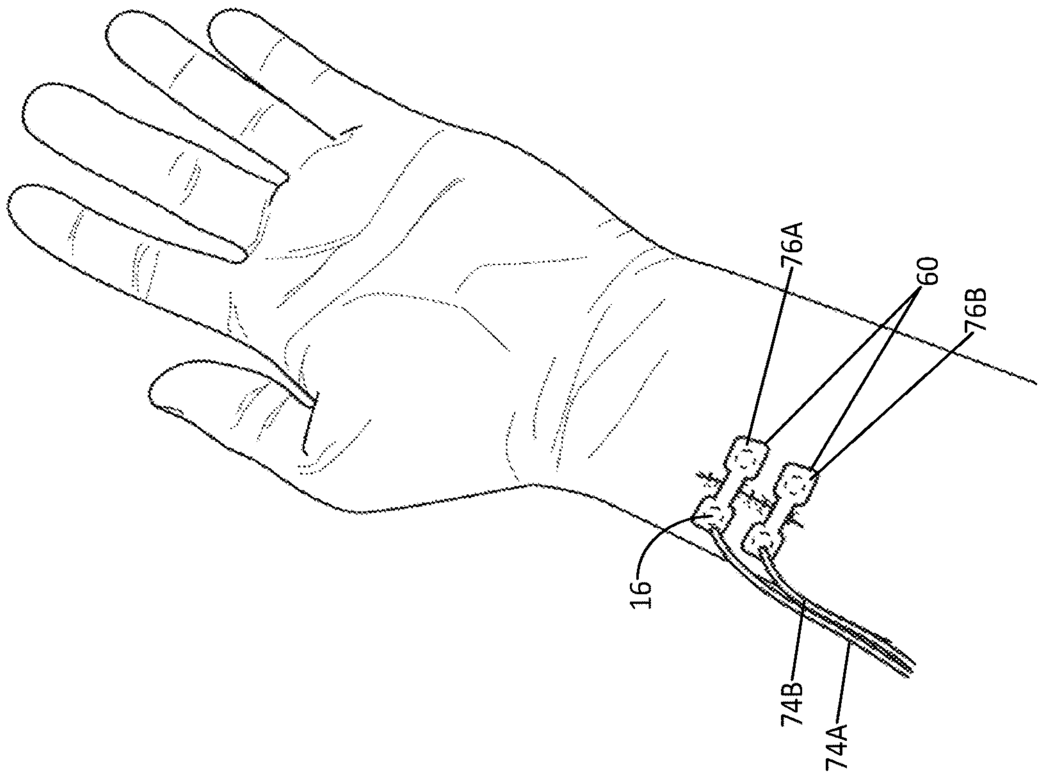

References here to an injury having "sides" does not imply any particular injury geometry. Further, another advantage of the strip-based embodiments of the electrode carrier 12 is that the strips 76A and 76B may be placed in a bridging arrangement with respect to the involved injury. FIG. 4C illustrates an example bridging embodiment, wherein the overall sheet 60 is divided into first and second strips 76A and 76B, where the strips 76A and 76B are placed in a bridging arrangement across the long axis of an elongate injury, here another closed surgical incision. In at least one such embodiment, the strips 76A and 76B are adhesive on the patient-facing surface 64 and are configured for use as wound-closure strips, with the added advantage of providing electrostimulation therapy for the bridged wound.

Broadly, an injury being "bridged" by respective electrodes 16 in the set 14 of electrodes 16 means that at least a portion of the injury intervenes or lies between the skin contact point of one electrode 16 relative to the skin contact point(s) of one or more other ones of the electrodes 16. Activating a given first electrode 16 as a signal source and, concurrently, activating a given second electrode 16 that is bridging with respect to the given first electrode 16 causes the electrical stimulation signal 22 to pass across or through the bridged portion of the injury. Of course, there may be multiple circuit paths between source and sink electrodes 16, in dependence on skin conductivity and subcutaneous impedances. As a general proposition, however, activating electrodes 16 that are bridging with respect to the injury results in the passage of the electrical stimulation signal 22 through the injured tissue.

FIG. 5 illustrates another example of the electrode carrier 12, where unique pairings 80 of electrodes 16 in the set 14 of electrodes 16 are used for electrical stimulation of an injury. The "pairings 80" are merely a specific case or example of the earlier-mentioned subsets 32. That is, a subset 32 may contain two electrodes 16 or more than two electrodes 16, whereas FIG. 5 illustrates the specific case of electrode pairings 80-1 through 80-7. At any given time, a first one of the electrodes 16 in a given pairing 80 is active as the signal source for the electrical stimulation signal 22 and a second one of the electrodes 16 in the pairing 80 is active as the signal sink for the electrical stimulation signal 22.

In at least some embodiments, the pairings 80 are bridging pairs of electrodes 16, at least nominally. That is, the stimulation module 18 may predefine which electrodes 16 of the electrode carrier 12 are operated as pairs 80, based on the underlying assumption that those electrodes 16 are "bridging" with respect to the involved injury (assuming a certain type or shape of injury and proper orientation of the electrode carrier 12 with respect to the injury). In other embodiments, the patient or the person treating the patient can designate which electrodes 16 are operated as pairs 80 or otherwise operated as subsets 32. Such designations may be input via the user interface 46 of the stimulation module 18, in one or more embodiments.

FIG. 6 illustrates an example activation sequence 82 provided by the signal generation circuitry 20 or as otherwise controlled or selected by the control circuitry 30. The depicted activation sequence 82 refers to the unique electrode pairings 80 illustrated in FIG. 5, but it should be understood that, in general, an activation sequence 82 specifies sequential activation of subsets 32 of electrodes 16, where the subsets 32 may include more than two electrodes 16 and where the subsets 32 may or may not have an equal number of members. As will be explained, an activation sequence 82 may be predefined or may be user-defined, although the activation sequence 82 depicted in FIG. 6 exploits the advantageous injury-bridging arrangement of electrode pairings 80 seen in FIG. 5.

Advantageously, in one or more embodiments, the activation sequence 82 "moves" the sources and sinks for the electrical stimulation signal 22 around the injury site, thereby creating spatially distributed signal paths through or across the injury over time. The activation sequence 82 may be predefined, e.g., selected from stored configuration data 40, or may be user-defined, e.g., determined via user inputs, or may be randomized by the control circuitry 30. A given activation sequence 82, randomized or not, does not necessarily guarantee that every subset 32 included in the activation sequence 82 contains electrodes 16 that are in a bridging relationship with respect to the injury.

FIG. 7 illustrates an example activation cycle 84, based on the example activation sequence 82 shown in FIG. 6. Specifically, FIG. 7 illustrates an activation cycle 84(*n*) that may be understood as one in series of one or more activation cycles 84(*n*−1), 84(*n*), 84(*n*+1) and so on. In general, a "treatment program" comprises an overall time in which the apparatus 10 provides therapeutic treatment to a patient, such that a treatment program may be understood as constituting a "session" and with the understanding that a patient may receive one session per day, one session per week, or multiple sessions per day, etc., in dependence on the injury type and desired overall treatment protocol. An overall collection of sessions—e.g., how many treatment programs the patient undergoes and interval between treatment programs—may be regarded as a "treatment regimen" or "treatment protocol."

In at least one embodiment, the apparatus 10 may be programmed for a desired treatment regimen defining the number and length of sessions, how often the sessions occur, along with optional further details like the type/size of electrode carrier 12 to be used, or stimulation-signal intensity, frequency, activation sequence or activation cycle definitions, etc. As such, a doctor or other knowledgeable person may program the apparatus 10 for a particular treatment regimen and send the patient home with the desired treatment regimen programmed in. For example, a patient having undergone facial surgery or other surgery where minimization of scarring is an acute concern may be provided with the apparatus 10, preprogrammed for a treatment regimen used expressly tailored for scarring reduction.

One area of programmability or adjustability involves the treatment program used by the apparatus 10. A treatment program may comprise one activation cycle 84, which steps through a defined activation sequence 82, using a controlled dwell time and step time. The dwell time refers to how long a given subset 32 is active within the activation sequence 82, and the step time refers to the delay between deactivating one subset 32 in the activation sequence 82 and activating the next subset 32 in the activation sequence 82. The dwell and step times may or may not be uniform throughout the sequence. Non-limiting examples of dwell and step times are thirty seconds and one second, respectively, and, as another point of flexibility, to the extent that a treatment program uses multiple activation sequences, essentially any operating parameter may be varied between sequences or within sequences. For example, the subset selections or subset order may be varied from activation cycle 84 to the next; that is, different activation sequences 82 may be used across multiple activation cycles 84. One or more activation cycles 84 thus constitute a treatment program or session.

With the above sequence/cycle examples in mind, in one or more embodiments, the control circuitry 30 is configured to sequentially activate the individual subsets 32 according to a defined activation sequence 82 that activates the individual subsets 32 one at a time, over a defined activation cycle 84. One or more other embodiments of the apparatus 10 provide for activating more than one subset 32 at a time.

In at least one embodiment, the defined activation sequence 82 is predefined and corresponds to a spatial arrangement of the set 14 of electrodes 16 on the body of the patient at the injury site that results from a specified placement of the electrode carrier 12 with respect to the injury site. That is, the spatial arrangement may or may not exist, in dependence on whether the electrode carrier 12 is positioned correctly on the body of the patient, or in dependence on whether the appropriate type, size, or model of electrode carrier 12 has been selected. However, as an example of a predefined activation sequence 82, FIG. 6 illustrates subsets 32—specifically, pairings 80—that correspond to electrodes 16 on opposing sides of the cutout 66 in the flexible sheet 60 that serves as the electrode carrier 12 in FIG. 5, with the assumption that the electrode carrier 12 will be placed on the body of the patient at the injury site, such that the injury lies within the skin area exposed by the cutout 66.

In other embodiments, or when operating in another mode, the control circuitry 30 is configured to determine the defined activation sequence 82 according to signaling received by the control circuitry 30. The signaling comprises, for example, any one of a signal 26 provided by or read from the electrode carrier 12, an input signal 50 resulting from user control of a control input provided by the stimulation module 18 (e.g., via the user interface circuitry 46), or an input signal 52 received via the I/O circuitry 48, or signaling 54 received via the communication circuitry 44. For example, the control circuitry 30 receives a wireless communication signal via the communication circuitry 44, from an external configuration device that is communicatively coupled to the stimulation module 18.

The individual subsets 32 comprise, such as in the example of FIG. 5, a plurality of electrode pairs 80, with each electrode pair 80 being a unique pairing of two electrodes 16 from the set 14 of electrodes 16 provided by the electrode carrier 12. One of the two electrodes 16 in each pairing 80 is operated as the signal source and the other one of the two electrodes 16 is operated as the signal sink. At least one among the plurality of electrode pairs 80, is at least putatively an "opposing" electrode pair 80 in which the two electrodes 16 have an opposing relationship in which at least a portion of an injury at the injury site intervenes between respective contact points of the two electrodes 16 on the body of the patient. In other words, at least one of the electrode pairs 80 at least putatively is in a bridging relationship with respect to the injury to be treated. "At least putatively" refers to embodiments of the apparatus 10 where the subsets 32/pairings 80 of electrodes 16 are fixed (predefined), such that whether they bridge the injury to be treated depends at least on proper placement of the electrode carrier 12 at the injury site.

Figure 8:
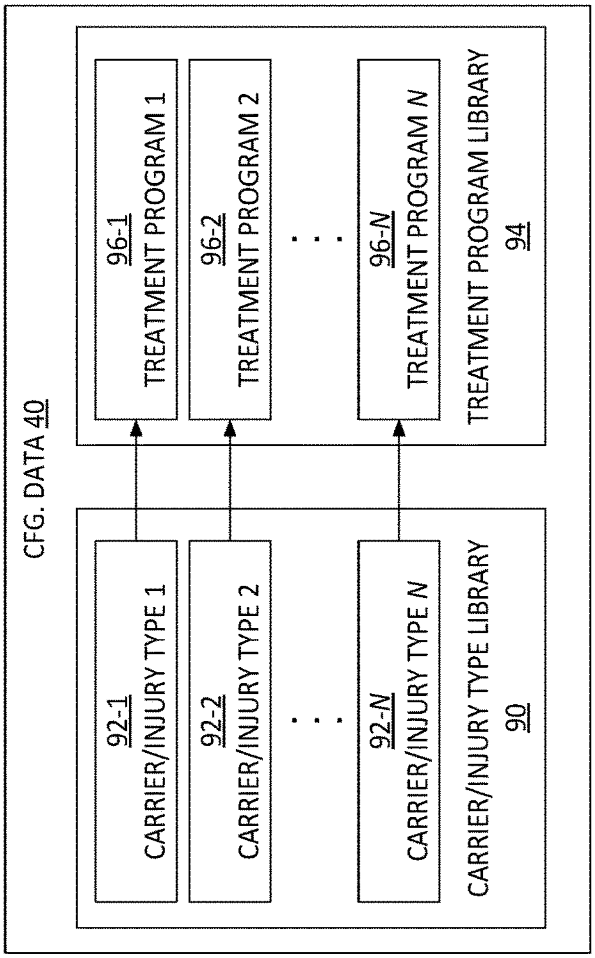
FIG. 8 is a diagram of example configuration data used by an electrostimulation apparatus, according to one or more embodiments.

FIG. 8 illustrates an example embodiment in which the configuration data 40 includes stored information, such as stored tables, that function as a carrier/injury type library 90 that maps different carrier/injury type entries 92 to different treatment programs 96 in a treatment program library 94. For example, the different carrier/injury type entries 92 correspond to different sizes of the set 14 of electrodes 16, or to different spatial arrangements of the electrodes 16 in the set 14. Alternatively, the different carrier/injury type entries 92 correspond to different types of injuries, such as torn muscles versus inflammatory conditions, or such as the size, shape, type, or depth of an invasive wound to be treated.

Correspondingly, then, the different treatment programs 96 in the treatment program library 94 distinguish from one another in any one or more of the following parameters: one or more parameters of the electrical stimulation signal 22, different definitions of the subsets 32, different definitions of the activation sequence 82, different definitions of the activation cycle 84, different numbers of activation-cycle repetitions to constitute the overall treatment program 96, etc.

In at least one embodiment, a user provides a selection input via a user interface of the stimulation module 18 to indicate the carrier type or injury type 92, with the control circuitry 30 correspondingly selecting the respective treatment program 96 that corresponds to the indicated carrier/injury type 92. In another embodiment, the user selects a particular treatment program 96 directly. This embodiment is advantageous, for example, in cases where the treatment programs 96 are predefined and optimized for particular kinds of ailments, such as "tennis elbow," wherein the duration of treatment, and the most advantageous pattern and timing of "movements" of the source/sink electrodes 16 around or over the affected area may be preprogrammed into the apparatus 10, based on empirical data.

Figure 9A:
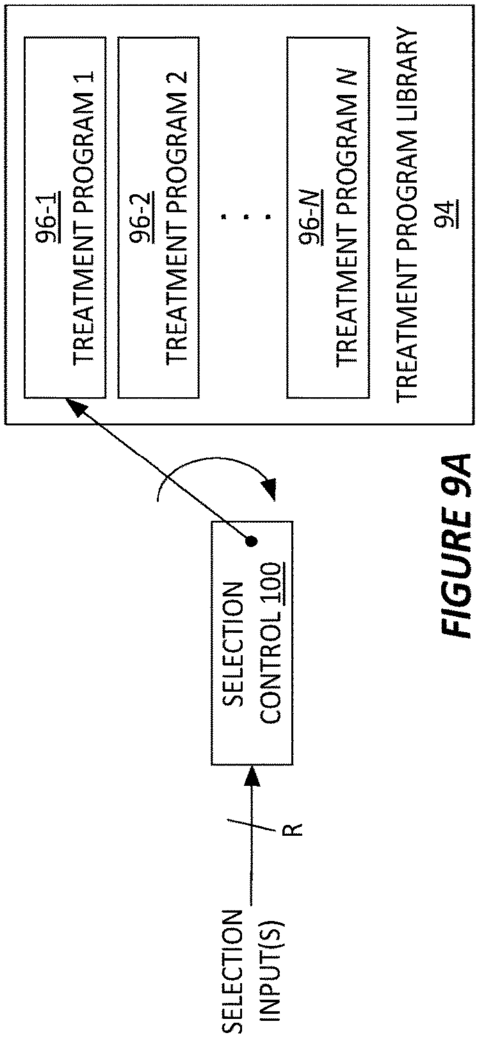
FIGS. 9A and 9B are diagrams of functional logic used by an electrostimulation apparatus for treatment program or treatment regimen selection, according to one or more embodiments.

FIG. 9A illustrates an example selection arrangement, wherein the control circuitry 30 implements a selection-control function 100 that selects a particular treatment program 96 from the treatment program library 94 in response to one or more selection inputs. Such inputs may indicate (directly or indirectly) the injury type and/or the electrode-carrier type. Again, "injury" has broad meaning, such that "injury type" may be broadly understood as referring to the type of injury or ailment to be treated.

Figure 9B:
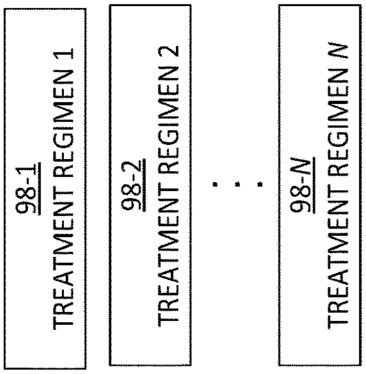

FIG. 9B shows that the same logic may additionally, or alternatively, be used for the selection of an overall treatment regimen 98, e.g., for selecting between defined treatment regimens 98-1, 98-2, and so on. Here, a treatment regimen 98 represents an overall course of treatment and, as such, defines, for example, the particular treatment program(s) 96 to be used by the apparatus 10, the length or timing of each treatment session, and the overall number or the frequency of treatment sessions. As an example, a given treatment regimen 98 is based on particular treatment program 96 being used, and it specifies five-minute treatment sessions using that particular treatment program 96, with three treatment sessions per day, over a total of five days. Again, in at least one embodiment, the apparatus 10 can be configured to use a particular treatment regimen 98, such that the patient need do no more than "connect" the electrode carrier 12 to the stimulation module 18 and put it on (or leave it on, in a "wearable" implementation of the electrode carrier 12).

Figure 10:
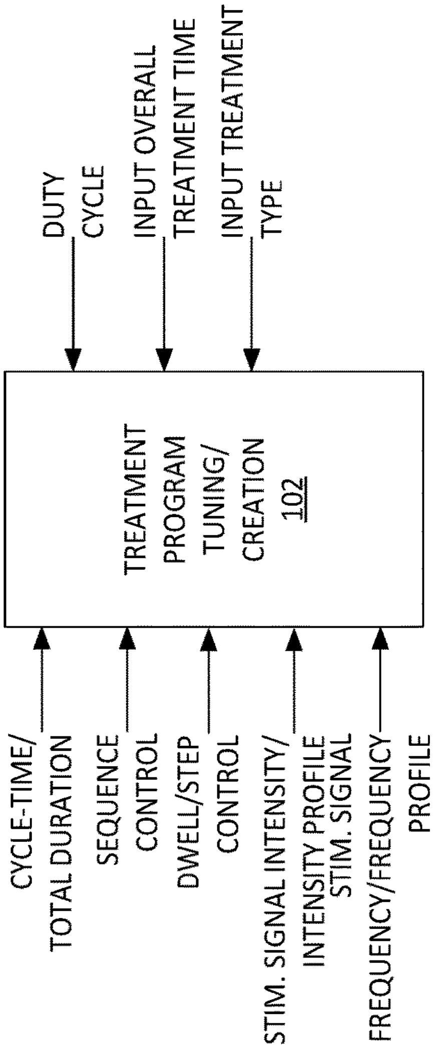
FIG. 10 is a diagram of functional logic used by an electrostimulation apparatus for treatment program creation or tuning, according to one or more embodiments.

FIG. 10 illustrates another functional circuit realized in the processing circuitry 30, namely, a treatment program tuning/creation function 102. With this function, the processing circuitry 30 is operative to create a treatment program 96, e.g., responsive to user input or responsive to received control signaling, or to modify ("tune") an existing treatment program 96. Creation/tuning parameters include any one or more of the following items: (a) cycle time of the activation cycle 84 or overall treatment time, e.g., how many cycle repetitions to use, (b) sequence selection, (c) dwell/step control, (d) stimulation signal intensity or intensity profile, e.g., over the course of one activation cycle 84, or over the course of the overall treatment session, (e) stimulation signal frequency or frequency profile, and (f) stimulation signal duty cycle, i.e., the duty cycle of the DC pulse train. Here, "intensity" refers to one or both of the stimulation signal current or voltage.

In at least one embodiment, the function 102 or other operational function of the control circuitry 30 provides a method by which a pair of electrodes 16 within the overall set 14 of electrodes 16 is chosen to be the source and sink electrodes for a specific amount of time before a new pair, which may include a previously used electrode 16, is chosen in similar fashion to be the source and sink electrodes 16 for an additional specific amount of time. This continues in sequence and this process is repeated as pre-determined by the treatment protocol defined by the programming or configuration of the stimulation module 18.

Further, in at least one such embodiment, the treatment provided by the apparatus 10 is tailored to the amount of time the user indicates is available for treating the patient—i.e., available for the currently contemplated treatment session. The user need only indicate the amount of time available for treatment and the control circuitry 30 optimizes the selection and pattern of activated source and sink electrodes 16 for the indicated amount of time made available. The control module 30 may impose boundaries, such as by enforcing a minimum treatment time required to initiate treatment activity at all.

For instance, referring back to the electrode carrier 12 illustrated in FIG. 3, the minimum treatment time may be six minutes, in an example embodiment. In the minimum (6 minutes) time setting, the control circuitry 30 activates electrodes L (Source) and D (sink) for one minute, then deactivates the L|D pairing and immediately activates electrodes K (source) and E (sink) for one minute; then deactivates the K|E pairing and immediately activates electrodes J (source) and K (sink) for one minute; then deactivates the J|K pairing and immediately activates electrodes A (source) and I (sink) for one minute; then deactivates the A|I pairing and immediately activates electrodes B (source) and H (sink) for one minute; then deactivates the B|H pairing, and, finally, activates electrodes C (source) and G (sink) for one minute.

Continuing the example, if the control circuitry 30 receives a user-input indication that 20 minutes is available for the treatment session, the control circuitry 30 uses a different pattern of activating the electrodes 16. For example, the control circuitry 30 directly (or indirectly through the signal generation circuitry 20) activates electrodes L (source) and D (sink) for two minutes, then deactivates the L|D pairing and immediately activates electrodes K (source) and E (sink) for two minutes; then deactivates the K|E pairing and immediately activates electrodes J (source) and K (sink) for two minutes; then deactivates the J|K pairing and immediately activates electrodes A (source) and I (sink) for two minutes; then deactivates the A|I pairing and immediately activates electrodes B (source) and H (sink) for two minutes; then deactivates the B|H pairing and immediately activates electrodes C (source) and G (sink) for two minutes; then deactivates the C|G pairing and immediately activates electrodes I (source) and F (sink) for one minute; then deactivates the I|F pairing and immediately activates electrodes J (source) and D (sink) for one minute; then deactivates the J|D pairing and immediately activates electrodes A (source) and G (sink) for one minute; then deactivates the A|G pairing and, finally, activates electrodes C (source) and I (sink) for one minute.

As time available for treatment expands, the control circuitry 30 or signal generation circuitry 20 is/are configured to use longer periods of activation for each electrode pairing and to use a greater number of different pairings, to push current through the injury area in as many different ways as possible. Thus, referring again to FIG. 3, as available time increases above 20 available minutes, activations may also include using activating electrodes L (source) and D (sink) for three minutes, but then leaving electrode L as the source and deactivating D (sink) and replacing it with E (sink) for an additional three minutes; and then leaving L as the source and deactivating E (sink) and replacing it with F (sink) for an additional three minutes. Other electrode groupings can likewise be alternated to create a "strobe" effect.

Figure 11:
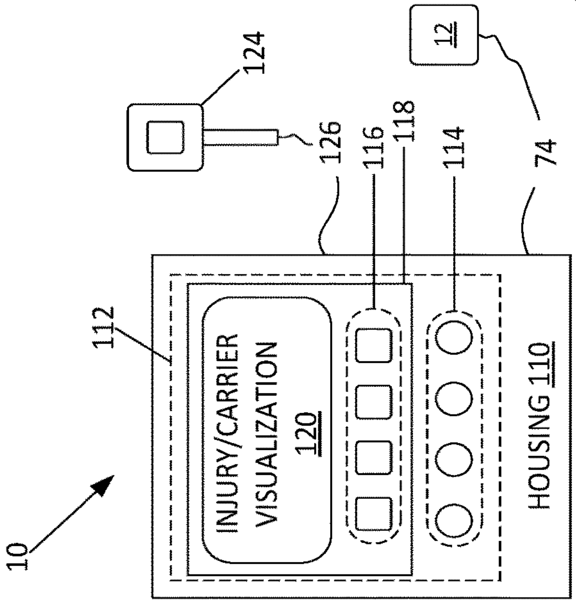
FIGS. 11 and 12 are block diagrams of an electro stimulation apparatus, according to another embodiment.

FIG. 11 illustrates another embodiment of the apparatus 10, wherein the apparatus 10 is at least partially housed in a housing 110, which includes a user interface 112, such as one or more physical control knobs or switches 114. Additionally, or alternatively, the user interface 112 provides one or more "soft" controls 116 displayed on a touch screen 118. The touch screen 118 in one or more embodiments is a video-capable screen that provides an injury/carrier visualization 120 onscreen. In at least one such embodiment, the apparatus 10 includes or provides an interface for a camera 124 for imaging the injury site on the body of the patient and for determining the placement or orientation of the electrode carrier 12 at the injury site.

Further, in at least one such embodiment, the injury/carrier visualization 120 includes onscreen depictions of the electrodes 16—e.g., video depictions of the electrodes or superimposed indications of their locations—and the control circuitry 30 is configured to define the subsets 32 of electrodes 16 based on receiving touch inputs from the user via the touchscreen 118. That is, the signal(s) provided to the control circuitry 30 via the user interface circuitry 46 may include touchscreen data, allowing the processing circuitry 30 to determine which electrodes 16 the user wishes to designate as belonging to a subset 32, based on the user directing touch inputs to the onscreen representations of the electrodes 16. Additionally, or alternatively, in one or more embodiments of the apparatus 10, the processing circuitry 30 is configured to receive touch inputs indicating which electrode(s) 16 in a subset 32 are source electrodes or sink electrodes.

The camera 124 may be dedicated to—specially adapted for—use with the apparatus 10 and in one or more embodiments is coupled to the apparatus 10 with a cable 126. In other embodiments, the camera 124 wirelessly couples to the apparatus 10 via the communication circuitry 44 included in the stimulation module 18. Similarly, although FIG. 11 suggests physical cabling between the electrode carrier 12 and the housing 110, the connection 24 may be wireless in one or more embodiments.

Figure 12:
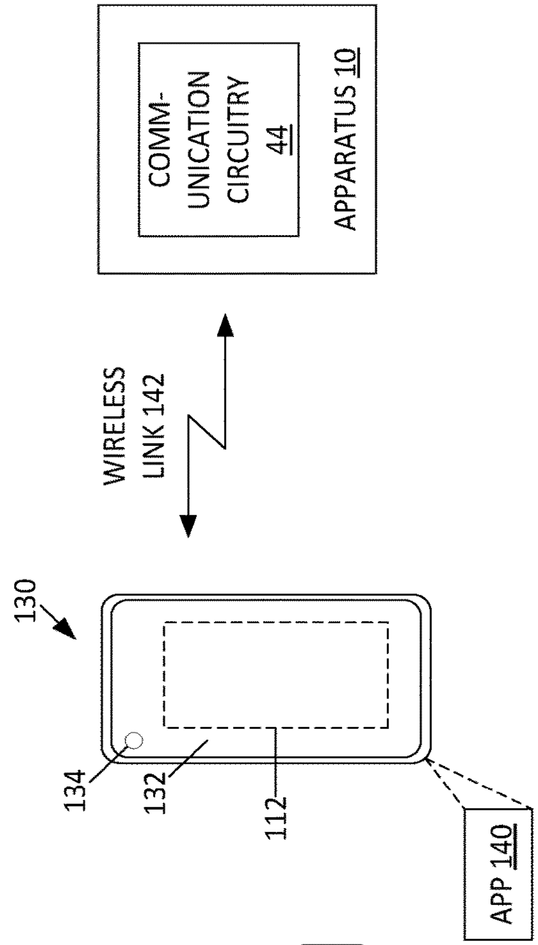

FIG. 12 illustrates yet another embodiment wherein all or a least a portion of the user interface 112 is realized on the screen 132 of an external device or system 130, such as a smartphone, tablet, laptop, or other computing device having a touch interface or other user-input capability. To the extent that the device 130 includes one or more cameras 134, the aforementioned body/injury visualization may be implemented within the device 130. Overall operation of the device 130 for supporting and interacting with the apparatus 10 is provided, for example, via the execution of a software app 140 that is installed from an app store or sideloaded into the device 130.

The communication circuitry 44 of the apparatus 10 provides a BLUETOOTH connection or other wireless link, for communicatively coupling to the device 130 via a wireless link 142, for establishing the connection 24 between the electrode carrier 12 and the stimulation module 18. Public Key Infrastructure (PKI) certificates, shared secrets, random nonces, or other security measures may be used between the apparatus 10 and the device 130, e.g., via the app 140, to ensure that connectivity and control is provided only to authorized devices 130.

Figure 13A:
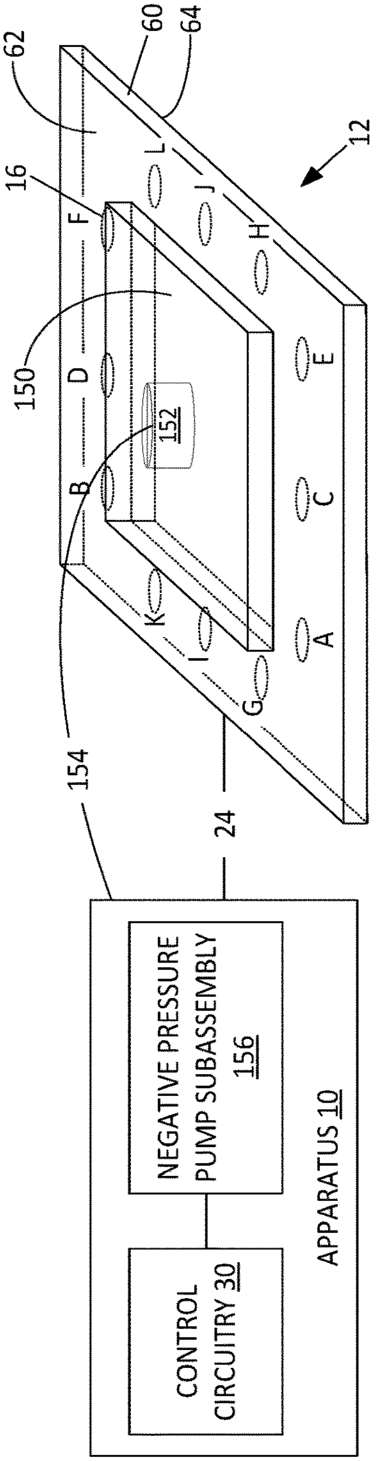
FIGS. 13A-13C are diagrams of an electrostimulation apparatus that integrates elements providing negative pressure treatment, according to another embodiment.

FIG. 13A illustrates yet another embodiment of the apparatus 10, wherein the electrode carrier 12 further comprises a sealable/sealed covering 150, covering the central cutout 66 of the flexible sheet 60. The covering 150 is ported for application of negative pressure to the injury, e.g., via a port 152 that couples via pneumatic tubing 144 to the apparatus 10, or to an associated vacuum apparatus. In at least one embodiment, the apparatus 10 incorporates the vacuum apparatus, shown in FIG. 13 as a negative pressure pump assembly 156.

Significant therapeutic synergies arise with the concurrent or coordinated application of negative pressure therapy and electrostimulation therapy. In one embodiment, the apparatus 10 coordinates the application of negative pressure, including the duration or extent of negative pressure developed within a "chamber" formed over the injury via the sealed cover 150. Note that the sealed cover 150 may be a separate membrane or sheet that adhesively couples to the underlying flexible sheet 60 comprising the electrode carrier 12. Such an arrangement offers flexibility in the sense that the sheet 60 can be sealed to the skin at the injury site, with the negative-pressure arrangement then "built" or otherwise applied onto the sheet 60.

In at least one embodiment of the apparatus 10 that includes negative pressure treatment, the treatment program(s) 96 implemented by the control circuitry 30 include negative pressure treatment protocols, e.g., defining any one or more of the duration of negative pressure application, the peak or average level of negative pressure applied, and the profile or variation in negative-pressure level used during the treatment session. Of course, in embodiments where the apparatus 10 has negative-pressure treatment capabilities, electrostimulation may be used with or without the concurrent use of negative-pressure treatment.

Figure 13B:
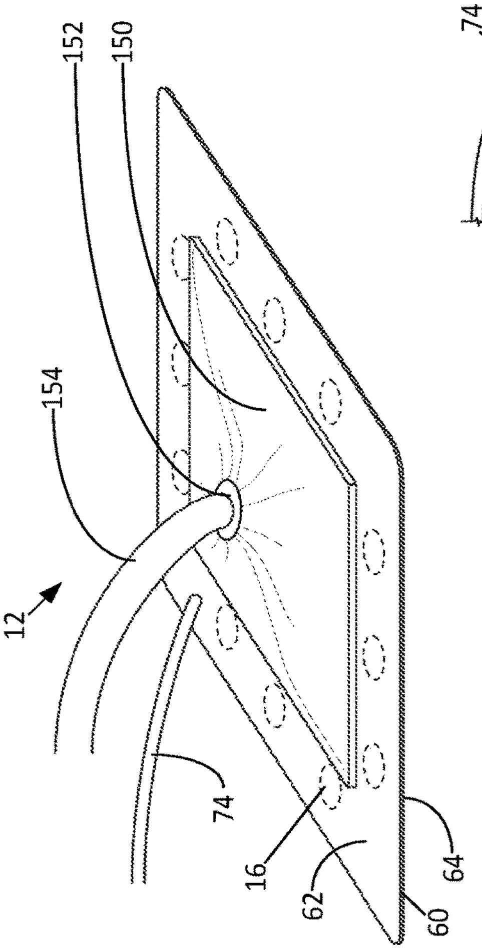
Figure 13C:
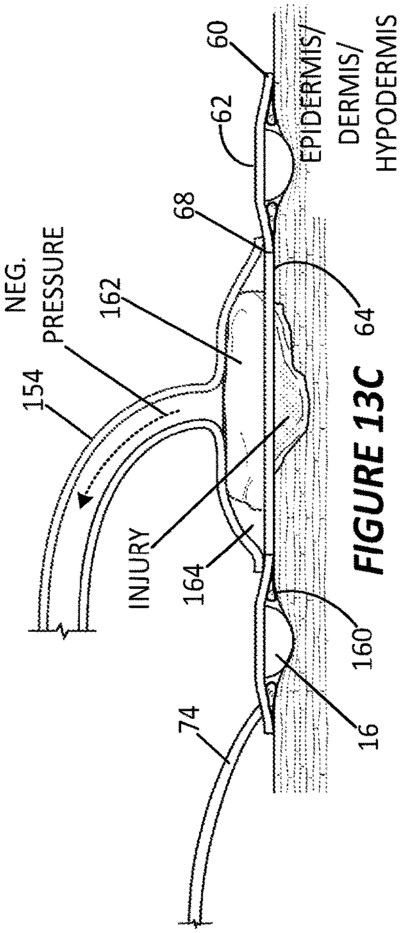

FIG. 13B offers another, more detailed view of the arrangement shown in FIG. 13A and FIG. 13C illustrates the same arrangement as applied to an injury on the body of the patient. Additional details shown in FIG. 13C include the adhesive 160 that may be pre-applied—e.g., a peel-off sticky cover—on the patient-facing surface 64 of the sheet 60, or that may be applied before the sheet 60 is placed onto the skin at the injury site. Further details include the use of a sterile sponge 162 or other packing material to establish support for the flexible covering 150 to form a negative-pressure chamber 164 at the injury site.

Figure 14A:
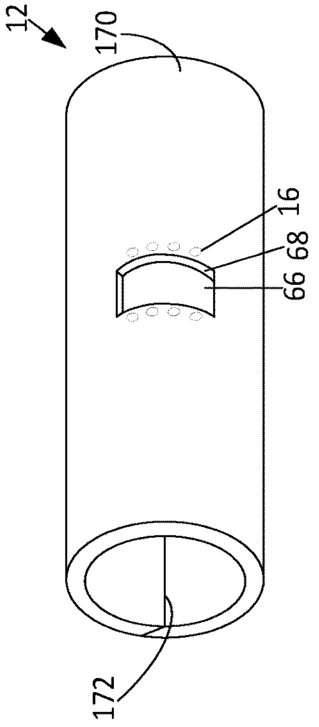
FIGS. 14A-14D are diagrams of an electrode carrier according to further example embodiments.

FIG. 14A illustrates an embodiment where the electrode carrier 12 is formed as a flexible sleeve 170 that is configured to encircle at least a portion of an affected limb of the patient. The sleeve at least optionally includes a cutout 66 to avoid covering the injury being treated. The sleeve may include a lengthwise split or seam 172, easing its installation on or removal from the affected limb. The sleeve 170 may be a fabric or plastic mesh or weave and may be elastic or use straps or hook-and-loop fasteners, for pressing the set 14 of electrodes 16 into a contacting arrangement with the skin of the patient at the injury site.

Figure 14B:
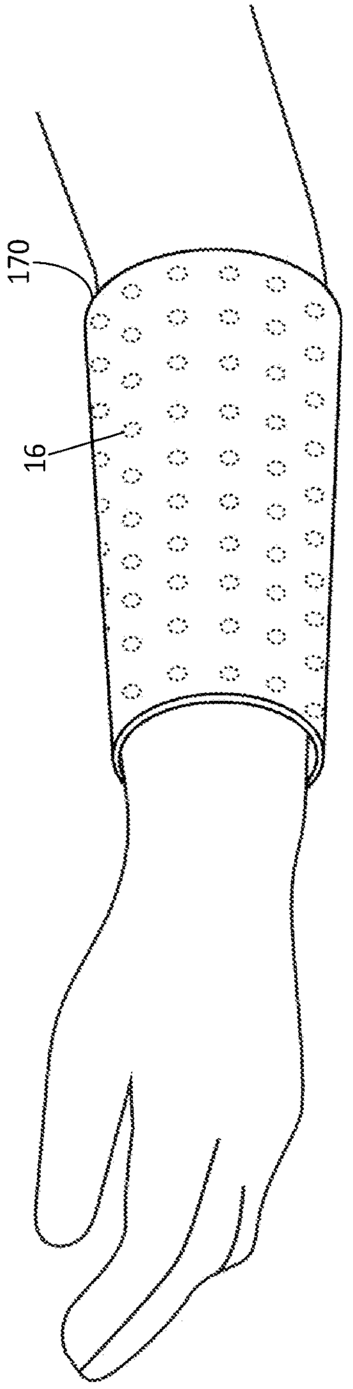

FIG. 14B illustrates another variation of the flexible sleeve 170, where the sleeve 170 omits the cutout 66 and where the set 14 of electrodes 16 are arrayed throughout the sleeve 170. Such an arrangement allows for creating/activating electrode subsets 32 all around the inner surface of the sleeve 170, and, therefore, allows one sleeve 170 to be used for treating different kinds and locations of injuries on the affected limb.

Figure 14D:
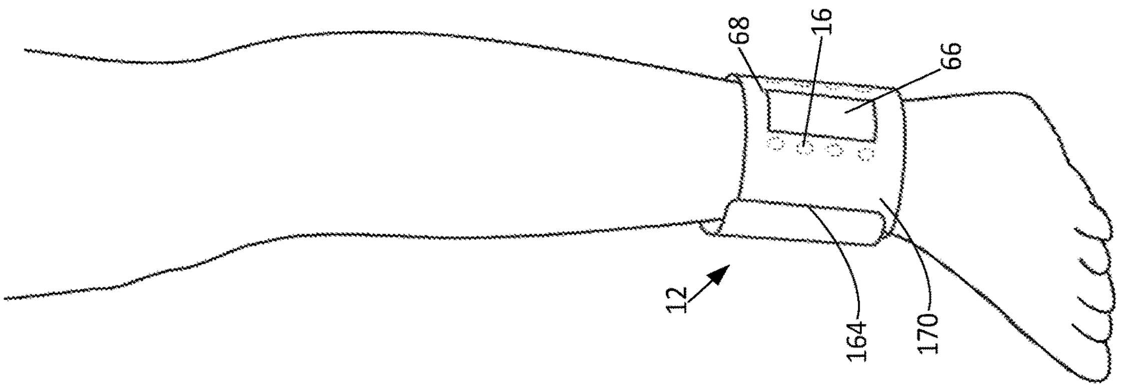
Figure 14C:
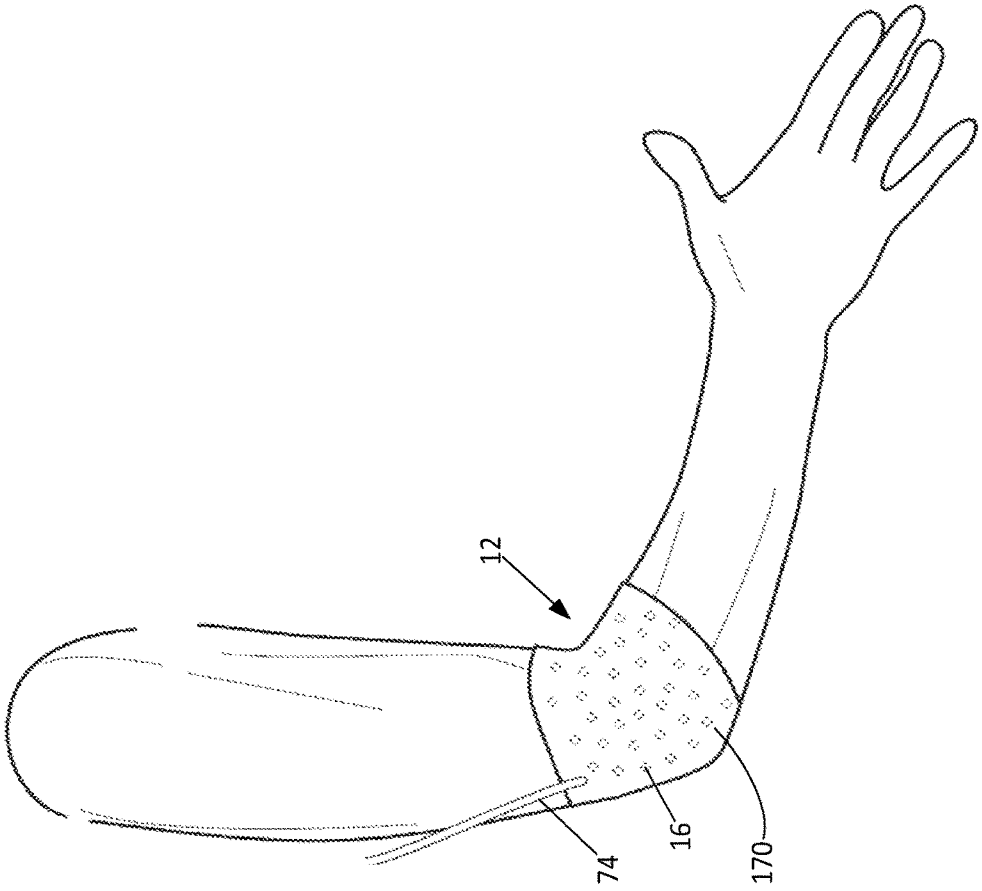

FIG. 14C illustrates a similar embodiment of the sleeve 170, but where the sleeve 170 is formed or contoured for use at a limb joint, with a (human) elbow sleeve shown as an example case. FIG. 14D illustrates another example case, where the sleeve 170 is configured for use on the ankle of a human leg, where this particular example uses a cutout 66. Other sleeve configurations are contemplated. For example, sleeves 170 may be configured for non-human limbs and joints, such as in the veterinarian context for treating leg injuries of dogs or cats. In a particularly compelling example of veterinarian use, the sleeve 170 in one or more embodiments is configured for use on the legs of horses, such as for treating hygroma, joint effusion, or other ailments commonly associated with racehorses.

Figure 15:
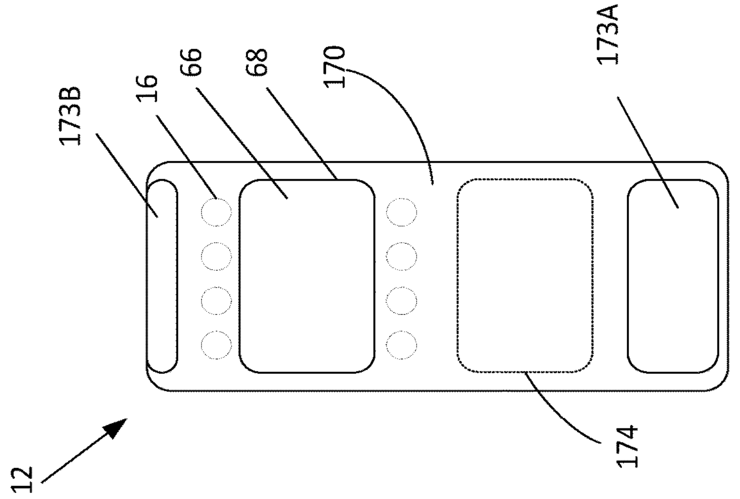

FIG. 15 illustrates another embodiment of the electrode carrier 12, wherein the sleeve 170 is shown as an encircling wrap that includes, for example, hook and loop fasteners 173A and 173B, to allow cinching the sleeve 170 in wrap-like fashion around the affected limb or, in at least some configurations, around the torso of the patient. Of course, snaps, buckles, or other accoutrements besides the hook and loop fasteners 173A/B may be used to secure the sleeve 170 in place.

Broadly, the sleeve 170 may be formed as one integral piece or may be made up of different pieces, potentially of different materials. For example, it may include a latex or polymer portion for contacting around the injury site and may include a fabric portion for cinching around the limb or torso.

In addition to using the hook and loop fasteners 173A/B (or alternative fasteners) for cinching the sleeve 170 in place, the sleeve 170 may include an internal sleeve or compartment for an inflatable bladder 174, similar to that used in blood-pressure cuffs. With the sleeve 170 cinched in place, inflating the bladder 174 causes the cinched sleeve 170 to tighten further against the body of the patient and thereby urge the electrodes 16 into better contact with the skin of the patient. Of course, the bladder 174 may have an overpressure valve or other mechanism to prevent overinflation and thereby guard against blood circulation problems or discomfort that might otherwise arise.

Figure 16:
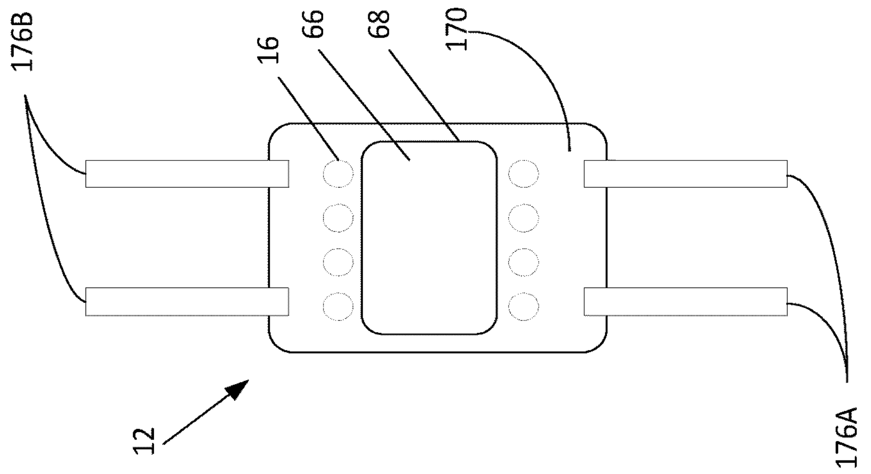
FIGS. 15 and 16 are diagrams of further example embodiments of an electrode carrier.

FIG. 16 illustrates a further variation of the electrode carrier 12, where the sleeve 170 includes straps 176A/B, which may have buckles or hook and loop fasteners, for strapping the sleeve 170 as a sleeve or encircling wrap around a limb or the torso of the patient.

Thus, in one or more embodiments, the electrode carrier 12 comprises some form of a compressive sleeve that exerts a biasing force urging the set 14 of electrodes 16 into contact with the body of the patient at the injury site. The arrangements in FIGS. 14A-D, 15, and 16 are examples formed or formable sleeves, offering biasing force obtained via at least one of: elastic material incorporated into the compressive sleeve, an inflatable bladder incorporated into the sleeve, or one or more cinching straps or fasteners incorporated into the sleeve.

FIGS. 17-20 illustrate example connectivity options in cases where the connection 24 between the electrode carrier 12 and the stimulus module 18 is a physical (wired) connection. Beginning with FIG. 17, the connection 24 in one or more embodiments includes a conductor 70 for each electrode 16 carried in the electrode carrier 12. While this arrangement offers simplicity and direct control regarding activating individual electrodes 16 as signal sources or sinks, such advantages come at the expense of potentially bulkier connection cables and more wiring.

Figure 18:
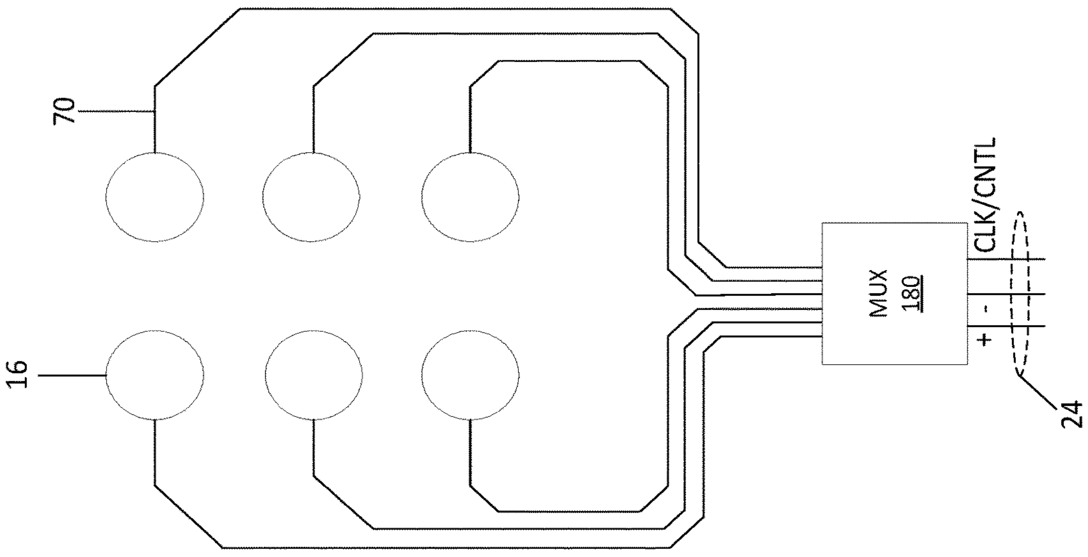
Figure 17:
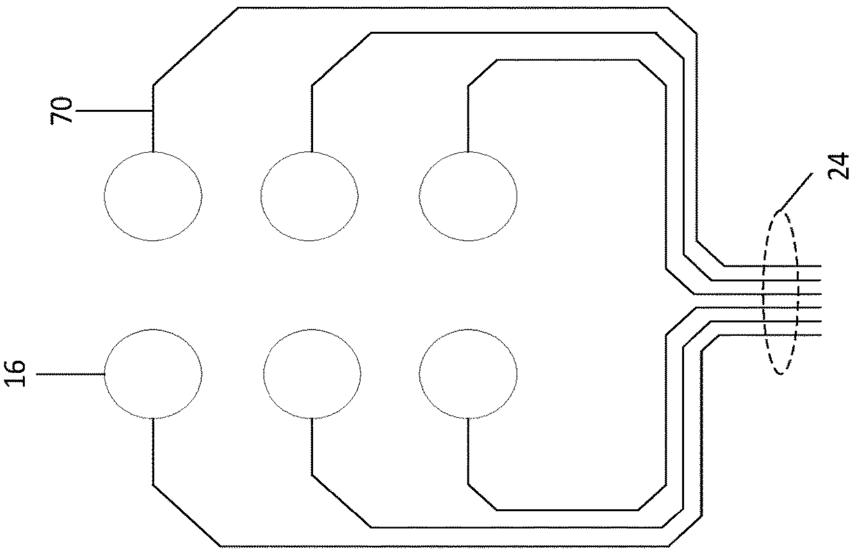

FIG. 18 illustrates another embodiment, where a multiplexer circuit 180 on the electrode carrier 12 reduces the wire count of the connection 24. For example, depending on the implementation of the multiplexer circuit 180, the connection 24 may include a signal source wire (+) and a signal sink wire (−) or "ground" connection, along with a clock/control signal ("CLK/CNTL"). A DC bias on the CLK/CNTL signal may be used to provide operating power for the multiplexer circuit 180, thus removing the need for the electrode carrier 12 to have its own power source for operating the multiplexer circuit 180.

Figure 19:
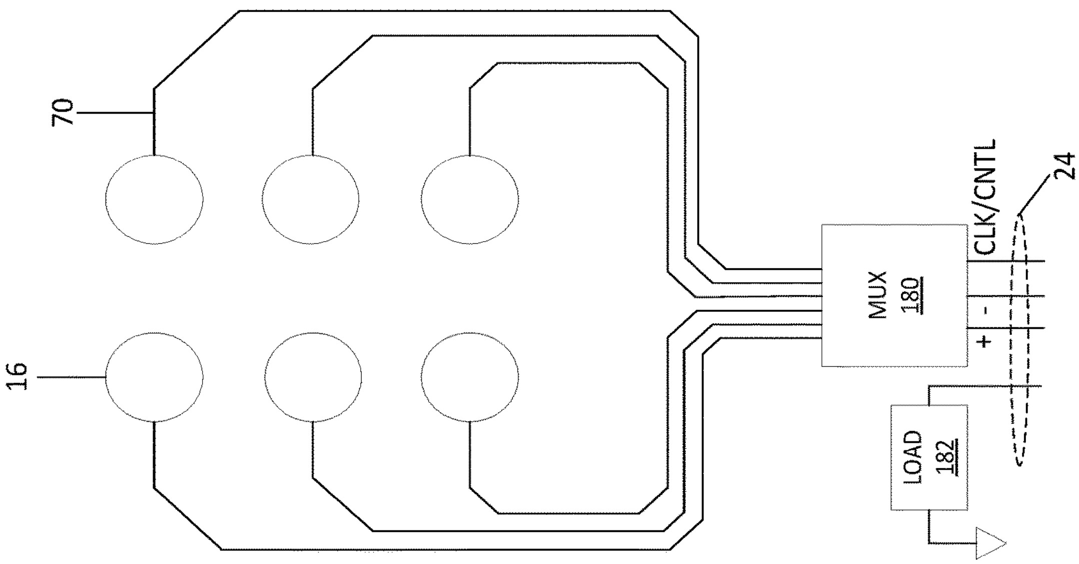
FIGS. 17-20 are block diagrams illustrating example interfaces between an electrode carrier and a stimulation module, according to various embodiments.

FIG. 19 illustrates substantially the same arrangement as depicted in FIG. 18, except that the electrode carrier 12 further includes a "load" circuit 182. The load circuit 182 may be as simple as a pull-down resistor that connects in voltage-divider fashion to a pull-up resistor in the stimulation module 18. Different values of pull-down resistors may be installed in different types or models of electrode carriers 12, thereby providing the control circuitry 30 with a simple mechanism for "reading" the type or model of electrode carrier 12 that is attached to it. Such information is used, for example, in selecting/defining the activation sequence 82 or activation cycle 84, or in selecting/defining the overall treatment program 96/treatment regimen 98, or in determining which treatment programs 96 or regimens 98 to offer for selection by the user.

In other variations, the load circuit 182 comprises a complex impedance, e.g., a notch or bandpass filter or resonant circuit. Correspondingly, the signal generation circuitry 20 of the stimulation module 18 is configured to generate an excitation signal at different frequencies corresponding to different types or models of the electrode carrier 12 and detect the response of the load circuit 182 at the different frequencies, for identifying the carrier type or model.

Figure 20:
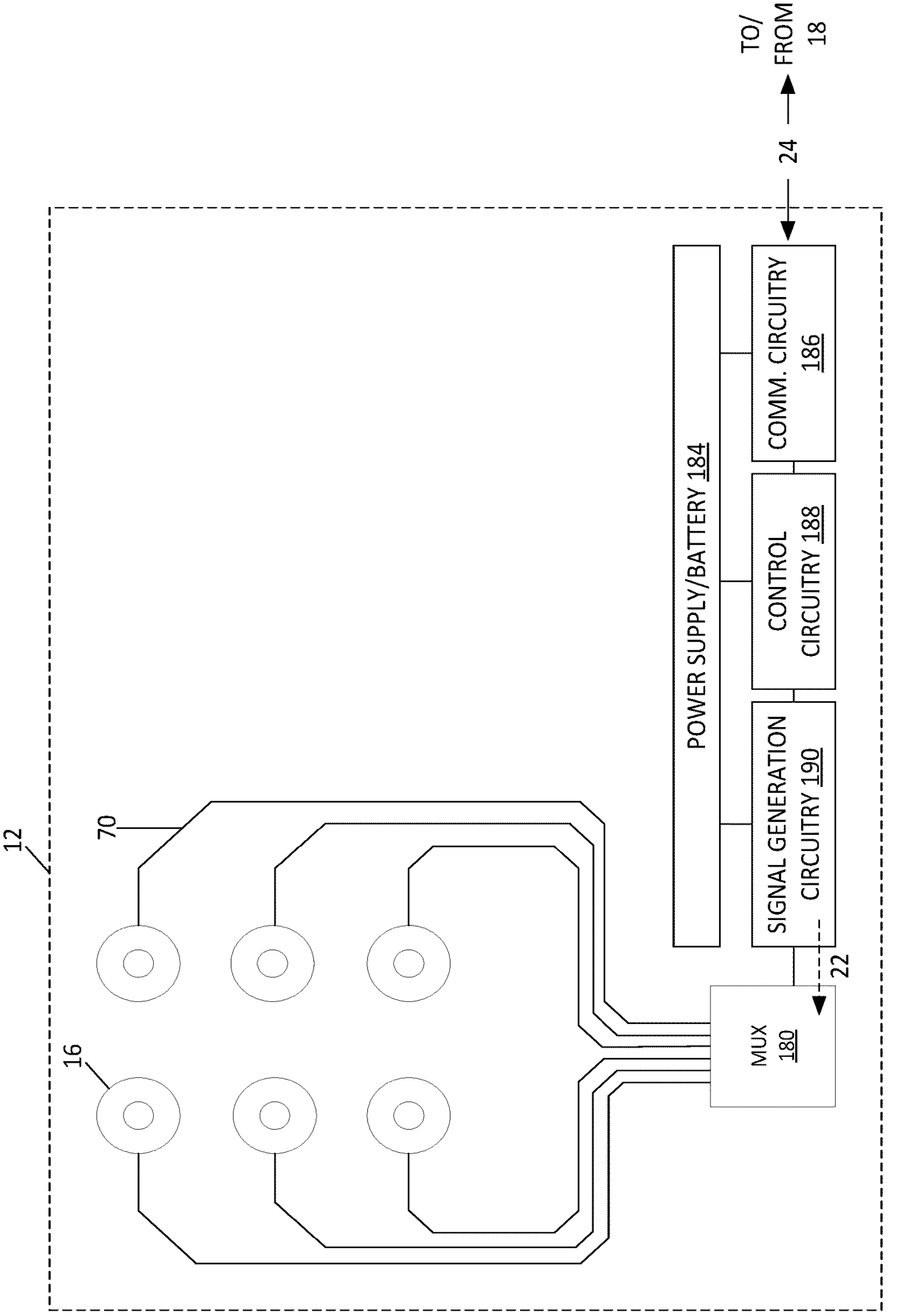

FIG. 20 illustrates yet another arrangement involving a more complex circuit implementation on the electrode carrier 12. Here, the connection 24 may be wired or wireless and the electrode carrier 12 has its own power supply/battery 184, for powering communication circuitry 186 that interfaces in wired or wireless fashion to the stimulation module 18. The electrode carrier 12 further includes control circuitry 188 that is responsive to signaling from the stimulation module 18, as received via the communication circuitry 186, such as start/stop control, etc.

Still further, the illustrated embodiment of the electrode carrier 12 includes signal generation circuitry 190. Thus, in at least one embodiment, generation of the electrical stimulation signal 22 occurs on the electrode carrier 12. In that regard, the signal generation circuitry 190 may be regarded as a version of the earlier-depicted signal generation circuitry 20 but moved from the stimulation module 18 over to the electrode carrier 12. Viewed another way, the circuitry depicted in FIG. 1 for the stimulation module 18 may be at least partially distributed between the electrode carrier 12 and a separate housing 110 that includes a user interface 112, etc.

Figure 21:
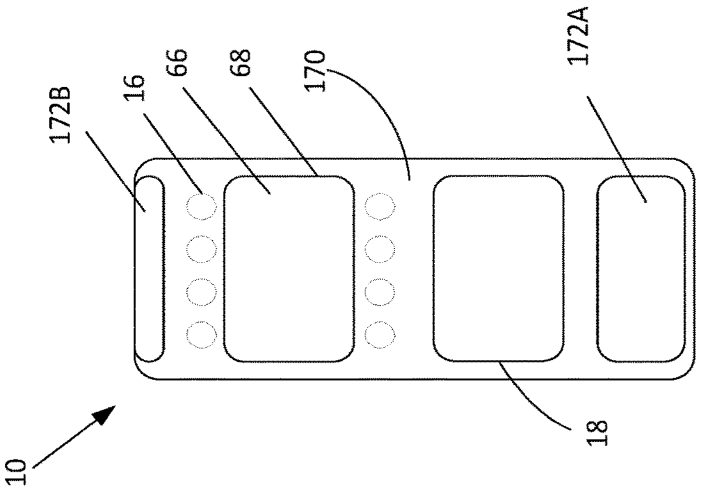
FIG. 21 is a block diagram of another embodiment of an electrostimulation apparatus, wherein an electrode carrier of the apparatus integrates a stimulation module of the apparatus.
Figures 23A, 23B, 23C, 23D:
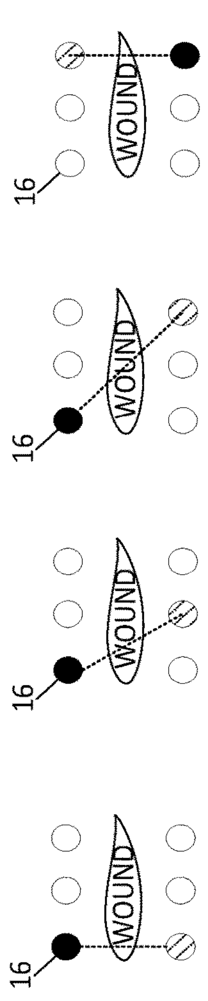
FIGS. 23A-23D illustrate an example "movement" pattern for distributing or sweeping an electrical stimulation signal across or through an injury at an injury site on the body of a patient.

FIG. 21 builds on the idea of local generation of the electrical stimulation signal 22 onboard the electrode carrier 12 by attaching the entirety of the stimulation module 18 on the electrode carrier 12. Here, the power supply/battery 42 of the stimulation module 18 comprises, for example, a lithium ion battery and associated charging and voltage-regulation circuitry, for battery-powered operation of the stimulation module 18. Further, the communication circuitry 44 may provide wireless connectivity to an external device 130, for implementation of a user interface 112 on the external device 130, for control of the apparatus 10.

Whether the stimulation module 18 is on or separate from the electrode carrier 12, the electrode carrier 12 in one or more embodiments comprises a flexible sheet 60 or sleeve 170. In at least one such embodiment, at least a portion of the patient-facing surface 64 of the sheet 60 or sleeve 170 is an adhesive membrane for temporary adhesion to the skin of the patient at the injury site. The adhesion provides, for example, for retaining the electrode carrier 12 on the body of the patient at the injury site, at least during the treatment, or for longer periods, such as several days during which the apparatus 10 provides multiple treatments, e.g., every four hours, automatically. In at least one embodiment, a sleeve 170 may be understood as including a sheet 60 serving as the base electrode carrier 12. That is, the sleeve 170 need not integrate the electrodes 16 directly, and instead can be understood as providing for the integration of a sheet 60 within its patient-facing interior surface, in a two-part assembly.

In any case, the use of an adhesive flexible membrane for carrying the electrodes 16 also provides for sealing engagement against the body of the patient. In turn, that sealing engagement provides for, for example, use of negative-pressure therapy in conjunction with electrostimulation, such as shown in FIGS. 13A-C.

In further example details, such as shown in FIG. 5, each electrode 16 in the set 14 of electrodes 16 may be considered as being a blunt contact-point electrode, such that bringing the set 14 of electrodes 16 into contact with the body of the patient defines a corresponding set of blunt contact points for point sourcing or sinking of the electrical stimulation signal 22. Among their various advantages as compared to distributed-area or "patch" electrodes, blunt contact-point electrodes can reduce impedance at the point of contact between the electrode 16 and the skin of the patient, which reduces signal losses with respect to "injection" of the electrical stimulation signal 22 into the body of the patient at the injury site. Plus, the use of discrete contact points allows for the patterning or moving of the electrical stimulation signal around and through the injury site.

Other operational advantages of the apparatus 10 include, in one or more embodiments, the signal generation circuitry 20 being configured to control the frequency of the electrical stimulation signal 22 responsive to control by the control circuitry 30. As an example, the control at issue is one of: selection of a particular frequency from among a set of predefined frequencies, continuous adjustment of the frequency, or stepped adjustment of the frequency. Additionally, or alternatively, the signal generation circuitry 20 may be configured to control an intensity of the electrical stimulation signal 22 responsive to control by the control circuitry 30. Here, the control is at least one of: adjustment of the voltage of the electrical stimulation signal 22, or adjustment of the current of the electrical stimulation signal 22.

Figure 22:
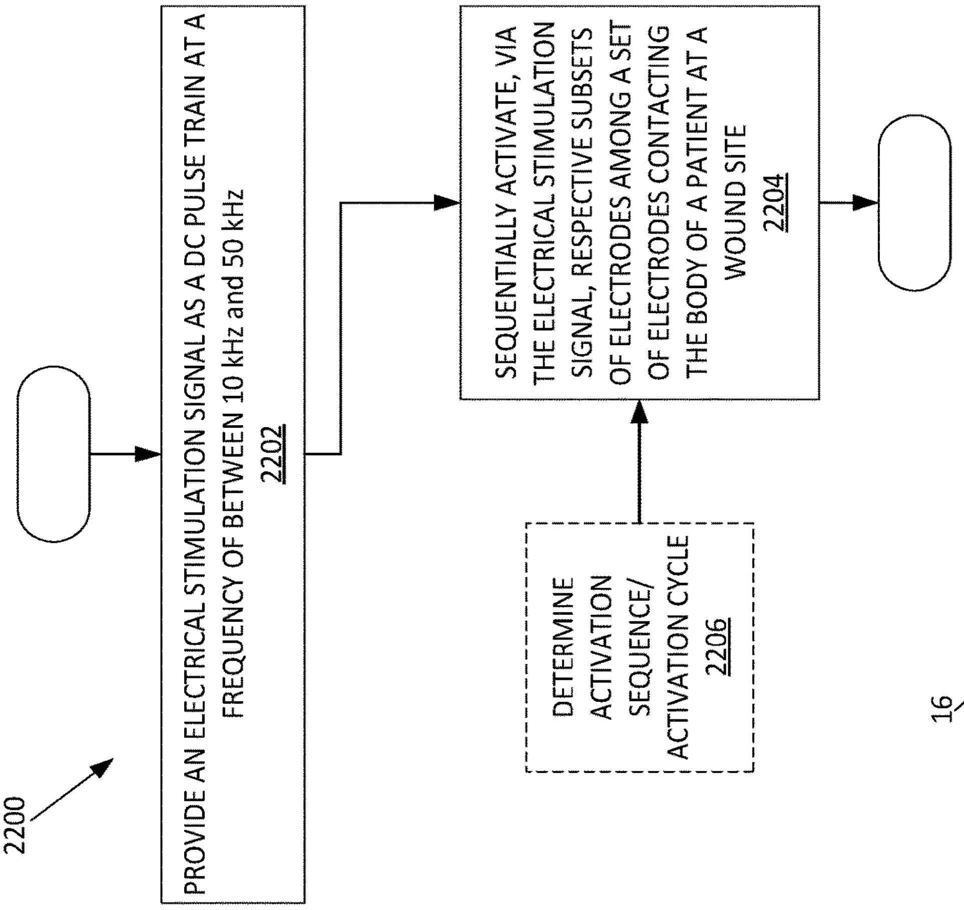
FIG. 22 is a logic flow diagram of a method performed by an electrostimulation apparatus according to one embodiment.

FIG. 22 illustrates one embodiment of a method 2200 for therapeutic electrical stimulation of a patient and may be performed by the apparatus 10 introduced in FIG. 1 or by another appropriately configured apparatus. The depicted operations may be performed in an order other than the order suggested by the logic flow and may be performed repeatedly or in conjunction with other operations.

The method 2200 includes providing (Block 2202) an electrical stimulation signal 22 as a Direct Current (DC) pulse train at a frequency of between 10 kHz and 50 kHz, and sequentially activating (Block 2204) respective subsets 32 of electrodes 16 among a set 14 of electrodes 16 contacting the body of the patient at an injury site on the body of the patient, via the electrical stimulation signal 22.

Sequentially activating the respective subsets 32 of electrodes 16 comprises, for example, activating the individual subsets 32 according to a defined activation sequence 82 that activates the individual subsets 32 one at a time, over a defined activation cycle 84. Thus, in one or more embodiments, the method 2200 also includes determining (Block 2206) the activation sequence 82 and/or activation cycle 84 to use for applying the electrical stimulation signal 22.

In at least one embodiment, the method 2200 further includes varying the defined activation sequence 82 or the defined activation cycle 84 responsive to user input received via a user interface 112 of the apparatus 10 or via the communication circuitry 44 of the apparatus 10.

The method 2200 may also include varying one or more parameters responsive to user input received via a user interface 112 of the apparatus 10 or via the communication circuitry 44 of the apparatus 10. The one or more parameters are, for example, any one or more of: a frequency of the electrical stimulation signal 22, a voltage of the electrical stimulation signal 22, a current of the electrical stimulation signal 22, or a duty cycle of the electrical stimulation signal.

In at least one embodiment of the method 2200, sequentially activating the respective subsets 32 of electrodes 16 comprises activating the respective subsets 32 of electrodes 16 according to a treatment program 96. The method 2200 may include obtaining the treatment program 96 as a pre-defined treatment program stored as configuration data 40 in the apparatus 10 or creating or tuning the treatment program 96 responsive to user input. As noted, the treatment program 96 dictates which electrodes 16 are activated at which times and for how long, and according to which electrical and timing parameters, and may define an overall duration of treatment and the sequence/repetitions of electrode activation.

Advantageously, the sequential activation of electrode subsets 32 as contemplated herein increases the efficacy of electrostimulation for injury healing by scanning or distributing the electrical stimulation signal 22 across or through the injury site. The scanning effectively "circulates" or "moves" the active contact points around the injury by sequentially changing which electrodes 16 are active as sources and sinks for the electrical stimulation signal 22, according to a defined activation sequence. FIGS. 23A-23D illustrate one such example of moving the signal sources and sinks around an injury.

In FIGS. 23A-23D, the black fill indicates which electrode 16 is active as a signal source and the black hatching indicates which electrode 16 is active as a signal sink. Although the figures show only one signal source and one signal sink at a time, there may be more than one source or sink active at a time, in dependence on how the subsets 32 are defined by the involved activation sequence 82.

Going from FIG. 23A to 23D, the signal source "moves" from left to right, relative to the depicted orientation of electrodes 16, as does the signal sink. Effectively, this sequence moves the contact points for the electrical stimulation signal 22 across or over the extent of the injury, going from left to right. As such, more of the injury is reached by the electrical stimulation signal 22, or, put another way, the electrical stimulation signal 22 is better distributed in and through the injury site, over time.

Figure 24:
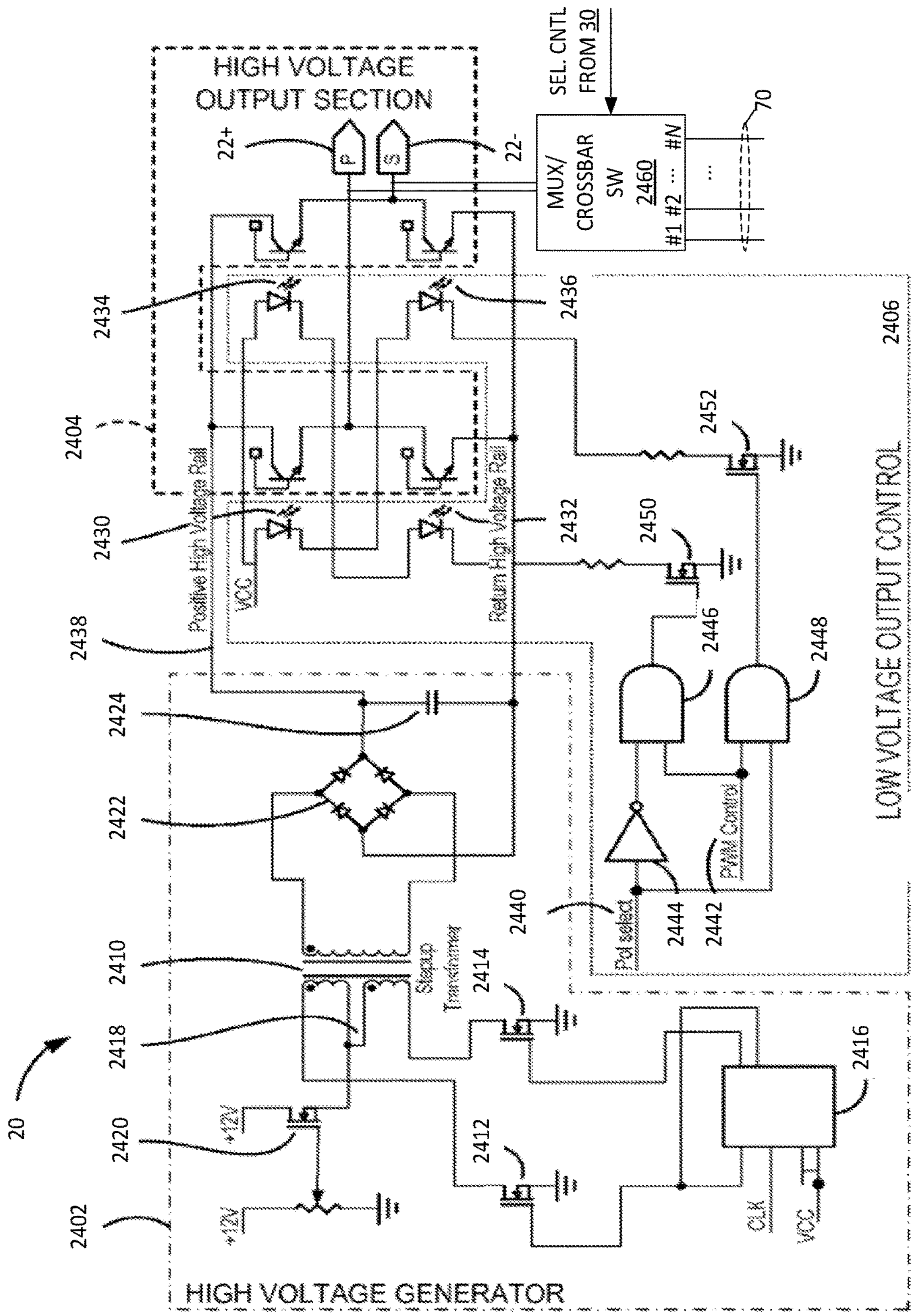
FIG. 24 is a schematic diagram of example signal generation circuitry according to one embodiment, for generating an electrical stimulation signal.

As for generation of the electrical stimulation signal 22, multiple arrangements are contemplated, and FIG. 24 offers a non-limiting example of one arrangement of the signal generation circuitry 20 for generation of the electrical stimulation signal.

The signal generation circuitry 20 operates as a pulse forming circuit that isolates the high voltage for the electrodes 16 from the lower voltage control circuits to produce a cleaner stimulus-signal waveform with better pulse shape free of ringing. The resulting unipolar waveform output promotes unidirectional ionic flow, which the empirical evidence suggests provides for more efficacious electrostimulation.

The illustrated circuitry includes a high voltage generator 2402, a high voltage output circuit 2404 and a low voltage output control circuit 2406, which provides for certain stimulation-signal tuning by the control circuitry 30.

The high voltage generator 2402 includes a step up transformer 2410, a set of MOSFETs 2412 and 2414 and a D flip flop 2416. A center tap input 2418 is coupled to a control MOSFET 2420 that is coupled to a DC voltage source such as the power supply battery 42 shown in FIG. 1. The secondary coil of the transformer 2410 is coupled to the inputs of a rectifier bridge 2422. The outputs of the rectifier bridge 2422 are coupled to a capacitor 2424. The high voltage that will be applied to the body is created by the transformer 2410 and then rectified by the bridge 2422 and stored on the capacitor 2424. The transformer 2410 in this example is relatively small and is driven by the push-pull circuit configuration composed of the primary coil of the transformer 2410, the MOSFETs 2412 and 2414 and the D flip flop 2416 which is driven by a clock input, e.g., at 40 kHz. A higher clock frequency allows a smaller transformer to be used.

The output voltage from the high voltage generator 2402 is a function of the center tap voltage coupled to the control MOSFET 2420 and the turns ratio of the transformer windings (primary to secondary turns). In the example arrangement illustrated, the output electrical stimulation signal 22 is obtained via the use of high voltage opto-isolators 2430, 2432, 2434, and 2436. Either the combination of opto-isolators 2430 and 2436 are used to output voltage to the electrodes 16 respectively, or to reverse the polarity, opto-isolators 2432 and 2434 are used to output voltage to the electrodes 16. The output of the high voltage generator 2402 is coupled to a positive high voltage rail 2438 that is controlled by the high voltage ends of the opto-isolators 2430, 2432, 2434, and 2436.

The selection of the stimulation-signal polarity is made via the low voltage output control circuit 2406. The low voltage output control circuit 2406 includes a polarity selection input 2440 and a pulse width modulation control input 2442, which are driven/controlled by the control circuitry 30.

The low voltage output control circuit includes an inverter 2444, AND gates 2446 and 2448, and output MOSFETs 2450 and 2452. The output MOSFET 2450 controls activation of the low voltage end of the opto-isolators 2432 and 2434 while the output MOSFET 2452 controls activation of the low voltage end of the opto-isolators 2430 and 2436. The polarity selection signal is received via the selection input 2440 and is directly coupled to one input of the AND gate 2446 and via the inverter 2444 to one input of the AND gate 2448. The output of the AND gates 2446 and 2448 drive the MOSFETs 2450 and 2452 respectively. The other input of the AND gates 2446 and 2448 are driven by a pulse width modulation control signal from the control input 2442. The pulse width control signal will time how long the output pulse is and at what frequency it is applied, and the control circuitry 30 is configured in one or more embodiments to set (or dynamically vary) the frequency of the electrical stimulation signal 22 to a frequency within the range of 10 kHz to 50 kHz.

Because the polarity selection signal is inverted to the AND gate 2446, only one set of opto-isolators 2430 and 2436 or 2432 and 2434 are activated to control high voltage output to the electrodes 16. The opto-isolation of the low voltage control from the high voltage provides a cleaner pulse shape output. The transformer parameters do not limit stimulation frequency or pulse width for the electrical stimulation signal 22 in the illustrated circuit configuration.

Example operating electrical parameters for the electrical stimulation signal 22 include: a 190 Volt peak pulse amplitude (unloaded electrodes 16), a 50-60 Volt pulse amplitude (loaded electrodes 16), 10 kHz to 50 kHz pulse frequency, fixed or variable duty cycle of the pulses in the pulse train, an output current of about 8.9 milliamps, and a maximum charge per pulse of 7 micro Coulombs.

Of course, one or more of these example signal parameters may be different or may be variable, in dependence on the particular electrical circuitry used to generate the electrical stimulation signal 22. Regardless of the circuitry used to generate the electrical stimulation signal 22, and other arrangements besides the one illustrated will be appreciated by those of ordinary skill in the art in view of the operational descriptions herein, one mechanism available for selectively connecting the electrical stimulation signal 22 to respective electrodes 16 to form activated subsets 32 of electrodes 16 is a multiplexing or crossbar switch circuit 2460. Such a switch provides for selective connection of the positive connection 22+ for the electrical stimulation signal 22 to any one or more of the conductors 70 that couple to the individual electrodes 16, and selective connection of the negative connection 22– for the electrical stimulation signal 22 to any one or more of the remaining ones of the conductors 70.

Notably, modifications and other embodiments of the disclosed invention(s) will come to mind to one skilled in the art having the benefit of the teachings presented in the foregoing descriptions and the associated drawings. Therefore, it is to be understood that the invention(s) is/are not to be limited to the specific embodiments disclosed and that modifications and other embodiments are intended to be included within the scope of this disclosure. Although specific terms may be employed herein, they are used in a generic and descriptive sense only and not for purposes of limitation.

What is claimed is:

1. An apparatus configured for therapeutic electrical stimulation of a patient, the apparatus comprising:

an electrode carrier configured to place a set of electrodes into contact with the body of the patient at an injury site on the body of the patient; and a stimulation module comprising:

signal generation circuitry-configured to generate an electrical stimulation signal as a Direct Current (DC) pulse train at a frequency of between 10 kHz and 50 kHz; and control circuitry that is configured to activate one or more individual subsets of electrodes in the set of electrodes, each subset including one or more electrodes activated as a signal source for the electrical stimulation signal and one or more electrodes-activated as a signal sink for the electrical stimulation signal, wherein the electrode carrier is configured for conformable placement on an exterior portion of the body of the patient at the injury site.

2. The apparatus in claim 1, wherein each subset of electrodes comprises a pair of electrodes.

3. The apparatus in claim 1, wherein the set of electrodes comprises a plurality of subsets of electrodes.

4. The apparatus in claim 3, wherein each of the plurality of subsets of electrodes comprises a pair of electrodes.

5. The apparatus in claim 3, wherein any one or more of the plurality of subsets of electrodes is connectable for a treatment regimen.

6. The apparatus in claim 3, wherein the control circuitry is configured to sequentially activate the plurality of subsets of electrodes.

7. The apparatus in claim 1, wherein the electrode carrier comprises a flexible sheet or membrane that conforms to the body of the patient at the injury site.

8. The apparatus in claim 1, wherein the electrode carrier has a top surface facing away from the body of the patient and a patient-facing surface that includes the set of electrodes.

9. The apparatus in claim 8, wherein the patient-facing surface of the electrode carrier comprises an adhesive.

10. The apparatus in claim 1, wherein the electrode carrier is wearable by the patient.

11. The apparatus in claim 1, wherein the electrode carrier comprises at least two plies.

12. The apparatus in claim 11, wherein wiring for the set of electrodes is embedded in the at least two plies.

13. The apparatus in claim 1, wherein the one or more electrodes in the one or more subsets of electrodes comprises a hemispherical tip.

14. The apparatus in claim 13, wherein the electrode carrier is formed as a wearable sleeve.

15. The apparatus in claim 14, wherein the wearable sleeve includes a cutout to avoid covering the injury site.

16. The apparatus in claim 14, wherein the one or more individual subsets of electrodes are arrayed throughout the wearable sleeve.

17. The apparatus in claim 14, wherein the wearable sleeve includes a flexible sleeve.

18. The apparatus in claim 14, wherein the wearable sleeve includes a strap.

19. The apparatus in claim 14, wherein the wearable sleeve includes a fastener.

20. The apparatus in claim 14, wherein the wearable sleeve includes a compartment.

* * * * *